United States Patent
Li et al.

(10) Patent No.: US 9,333,297 B2
(45) Date of Patent: *May 10, 2016

(54) DRUG-DELIVERY PUMP WITH INTELLIGENT CONTROL

(71) Applicants: Po-Ying Li, Monrovia, CA (US); Shengtao Li, La Puente, CA (US); Jonathan K. Lee, Montebello, CA (US); Patrick Ryan, Los Angeles, CA (US); Alice Lai, Pasadena, CA (US); Sean Caffey, Pasadena, CA (US); Mark S. Humayun, Glendale, CA (US)

(72) Inventors: Po-Ying Li, Monrovia, CA (US); Shengtao Li, La Puente, CA (US); Jonathan K. Lee, Montebello, CA (US); Patrick Ryan, Los Angeles, CA (US); Alice Lai, Pasadena, CA (US); Sean Caffey, Pasadena, CA (US); Mark S. Humayun, Glendale, CA (US)

(73) Assignee: MiniPumps, LLC, Pasadena, CA (US)

(*) Notice: Subject to any disclaimer, the term of this patent is extended or adjusted under 35 U.S.C. 154(b) by 157 days.

This patent is subject to a terminal disclaimer.

(21) Appl. No.: 14/035,835

(22) Filed: Sep. 24, 2013

(65) Prior Publication Data

US 2014/0094771 A1 Apr. 3, 2014

Related U.S. Application Data

(63) Continuation-in-part of application No. 12/858,808, filed on Aug. 18, 2010, now Pat. No. 9,199,035, which is a continuation-in-part of application No. 12/463,265, filed on May 8, 2009.

(Continued)

(51) Int. Cl.
*A61M 5/168* (2006.01)
*A61M 5/172* (2006.01)

(Continued)

(52) U.S. Cl.
CPC ............... *A61M 5/172* (2013.01); *A61M 5/148* (2013.01); *A61M 5/14244* (2013.01);

(Continued)

(58) Field of Classification Search
CPC . A61M 5/172; A61M 5/1723; A61M 5/3146; A61M 2005/1402; A61M 5/14244; A61M 5/14248; A61M 5/14276; A61M 5/16804; A61M 5/16809; A61M 5/16854; A61M 2005/14252; A61M 2205/3341; A61M 2205/3334; A61M 2205/3331; A61M 2205/3368; A61M 2205/50; A61M 2205/0222; A61M 2205/0238; A61M 2205/8206; A61M 2205/8293; A61M 31/002; A61M 2210/0693; A61M 2210/0612; G06F 19/3468

See application file for complete search history.

(56) References Cited

U.S. PATENT DOCUMENTS 2,445,477 A 7/1948 Folkman
3,175,558 A 3/1965 Caillonette et al.

(Continued)

FOREIGN PATENT DOCUMENTS

CN 1321096 A 11/2001
CN 102576385 A 7/2012

(Continued)

OTHER PUBLICATIONS

Examination Report Received for Mexican Patent App. No. MX/A/2012/012133 mailed on Sep. 25, 2014.

(Continued)

*Primary Examiner* — Bhisma Mehta
*Assistant Examiner* — Jenna Zhang
(74) *Attorney, Agent, or Firm* — Morgan, Lewis & Bockius LLP

(57) ABSTRACT

Embodiments of the present invention utilize a closed-loop feedback control system to ensure accurate drug delivery. This control system may, for example, utilize a flow sensor to measure the volume of delivery and an intelligent control algorithm to anticipate and compensate for overdoses and underdoses. Feedback control systems in accordance herewith can be applied to any piston- or plunger-driven pump system utilizing sensors that measure flow directly or indirectly. In some embodiments, adjustments are made based on the flow "tail" that occurs in a piston- or plunger-type pump as relaxation of the plunger material continues to push fluid out of the drug reservoir; this residual flow eventually ceases after the plunger returns to its natural state.

14 Claims, 8 Drawing Sheets

Related U.S. Application Data

(60) Provisional application No. 61/051,422, filed on May 8, 2008, provisional application No. 61/197,751, filed on Oct. 30, 2008, provisional application No. 61/197,769, filed on Oct. 30, 2008, provisional application No. 61/198,131, filed on Nov. 3, 2008, provisional application No. 61/198,090, filed on Nov. 3, 2008, provisional application No. 61/234,742, filed on Aug. 18, 2009, provisional application No. 61/704,946, filed on Sep. 24, 2012.

(51) Int. Cl.
| | | |
|---|---|---|
| *A61M 5/31* | (2006.01) | |
| *A61M 5/142* | (2006.01) | |
| *A61M 5/148* | (2006.01) | |
| *G06F 19/00* | (2011.01) | |
| *A61M 5/155* | (2006.01) | |
| *A61M 5/145* | (2006.01) | |
| *A61M 31/00* | (2006.01) | |

(52) U.S. Cl.
CPC ...... *A61M 5/14248* (2013.01); *A61M 5/14276* (2013.01); *A61M 5/14526* (2013.01); *A61M 5/16804* (2013.01); *A61M 5/16809* (2013.01); *A61M 5/3146* (2013.01); *G06F 19/3468* (2013.01); *A61M 5/14586* (2013.01); *A61M 5/14593* (2013.01); *A61M 5/155* (2013.01); *A61M 5/16854* (2013.01); *A61M 31/002* (2013.01); *A61M 2005/14204* (2013.01); *A61M 2005/14252* (2013.01); *A61M 2005/14513* (2013.01); *A61M 2205/0222* (2013.01); *A61M 2205/0238* (2013.01); *A61M 2205/3331* (2013.01); *A61M 2205/3334* (2013.01); *A61M 2205/3341* (2013.01); *A61M 2205/3368* (2013.01); *A61M 2205/50* (2013.01); *A61M 2205/8206* (2013.01); *A61M 2205/8231* (2013.01); *A61M 2205/8293* (2013.01); *A61M 2210/0612* (2013.01); *A61M 2210/0693* (2013.01)

(56) References Cited

U.S. PATENT DOCUMENTS

| | | |
|---|---|---|
| 3,731,681 A | 5/1973 | Blackshear et al. |
| 3,760,805 A | 9/1973 | Higuchi |
| 3,894,538 A | 7/1975 | Richter |
| 3,916,899 A | 11/1975 | Theeuwes |
| 3,977,404 A | 8/1976 | Theeuwes |
| 4,140,121 A | 2/1979 | Kuhl et al. |
| 4,140,122 A | 2/1979 | Kuhl et al. |
| 4,150,673 A | 4/1979 | Watt |
| 4,164,560 A | 8/1979 | Folkman et al. |
| 4,180,375 A | 12/1979 | Magnussen |
| 4,203,441 A | 5/1980 | Theeuwes |
| 4,237,881 A | 12/1980 | Beigler et al. |
| 4,300,554 A | 11/1981 | Hessberg et al. |
| 4,373,527 A | 2/1983 | Fischell |
| 4,543,088 A | 9/1985 | Bootman et al. |
| 4,553,973 A | 11/1985 | Edgren |
| 4,692,145 A | 9/1987 | Weyant |
| 4,738,657 A | 4/1988 | Hancock et al. |
| 4,751,926 A | 6/1988 | Sasaki |
| 4,760,837 A | 8/1988 | Petit |
| 4,781,675 A | 11/1988 | White |
| 4,781,695 A | 11/1988 | Dalton |
| 4,838,887 A | 6/1989 | Idriss |
| 4,853,224 A | 8/1989 | Wong |
| 4,886,499 A | 12/1989 | Cirelli et al. |
| 4,886,514 A | 12/1989 | Maget |
| 4,888,176 A | 12/1989 | Langer et al. |
| 4,902,278 A | 2/1990 | Maget et al. |
| 4,923,457 A | 5/1990 | Ellingsen |
| 4,944,659 A | 7/1990 | Labbe et al. |
| 4,959,217 A | 9/1990 | Sanders et al. |
| 4,969,874 A | 11/1990 | Michel et al. |
| 5,062,834 A | 11/1991 | Gross et al. |
| 5,066,276 A | 11/1991 | Wang |
| 5,067,491 A | 11/1991 | Taylor et al. |
| 5,090,963 A | 2/1992 | Gross et al. |
| 5,108,372 A | 4/1992 | Swenson |
| 5,135,498 A | 8/1992 | Kam et al. |
| 5,135,499 A | 8/1992 | Tafani et al. |
| 5,147,647 A | 9/1992 | Darougar |
| 5,163,909 A | 11/1992 | Stewart |
| 5,164,188 A | 11/1992 | Wong |
| 5,171,213 A | 12/1992 | Price, Jr. |
| 5,178,604 A | 1/1993 | Baerveldt et al. |
| 5,207,227 A | 5/1993 | Powers |
| 5,213,568 A | 5/1993 | Lattin et al. |
| 5,242,406 A | 9/1993 | Gross et al. |
| 5,242,408 A | 9/1993 | Jhuboo et al. |
| 5,252,192 A | 10/1993 | Ludwig |
| 5,279,607 A | 1/1994 | Schentag et al. |
| 5,318,540 A | 6/1994 | Athayde et al. |
| 5,318,557 A | 6/1994 | Gross |
| 5,354,264 A | 10/1994 | Bae et al. |
| 5,368,571 A | 11/1994 | Horres, Jr. |
| 5,399,166 A | 3/1995 | Laing |
| 5,407,441 A | 4/1995 | Greenbaum |
| 5,425,716 A | 6/1995 | Kawasaki et al. |
| 5,443,505 A | 8/1995 | Wong et al. |
| 5,458,095 A | 10/1995 | Post et al. |
| 5,462,739 A | 10/1995 | Dan et al. |
| 5,472,436 A | 12/1995 | Fremstad |
| 5,474,527 A | 12/1995 | Bettinger |
| 5,476,445 A | 12/1995 | Baerveldt et al. |
| 5,505,697 A | 4/1996 | McKinnon et al. |
| 5,527,288 A | 6/1996 | Gross et al. |
| 5,553,741 A | 9/1996 | Sancoff et al. |
| 5,616,219 A | 4/1997 | Patterson |
| 5,629,008 A | 5/1997 | Lee |
| 5,676,651 A | 10/1997 | Larson, Jr. et al. |
| 5,697,153 A | 12/1997 | Saaski et al. |
| 5,704,520 A | 1/1998 | Gross |
| 5,707,499 A | 1/1998 | Joshi et al. |
| 5,713,857 A | 2/1998 | Grimard et al. |
| 5,725,017 A | 3/1998 | Elsberry et al. |
| 5,725,493 A | 3/1998 | Avery et al. |
| 5,741,275 A | 4/1998 | Wyssmann |
| 5,782,799 A | 7/1998 | Jacobsen et al. |
| 5,785,688 A | 7/1998 | Joshi et al. |
| 5,788,682 A * | 8/1998 | Maget ............... A61F 13/00063 604/290 |
| 5,798,114 A | 8/1998 | Elsberry et al. |
| 5,798,115 A | 8/1998 | Santerre et al. |
| 5,800,420 A | 9/1998 | Gross et al. |
| 5,824,072 A | 10/1998 | Wong |
| 5,830,173 A | 11/1998 | Avery et al. |
| 5,836,935 A | 11/1998 | Ashton et al. |
| 5,868,697 A | 2/1999 | Richter et al. |
| 5,891,097 A | 4/1999 | Saito et al. |
| 5,904,144 A | 5/1999 | Hammang et al. |
| 5,951,538 A | 9/1999 | Joshi et al. |
| 5,989,579 A | 11/1999 | Darougar et al. |
| 5,993,374 A | 11/1999 | Kick |
| 5,993,414 A | 11/1999 | Haller |
| 6,048,328 A | 4/2000 | Haller et al. |
| 6,129,696 A | 10/2000 | Sibalis |
| 6,144,106 A | 11/2000 | Bearinger et al. |
| 6,203,523 B1 | 3/2001 | Haller et al. |
| 6,240,962 B1 | 6/2001 | Tai et al. |
| 6,251,090 B1 | 6/2001 | Avery et al. |
| 6,254,586 B1 | 7/2001 | Mann et al. |
| 6,264,971 B1 | 7/2001 | Darougar et al. |
| 6,281,192 B1 | 8/2001 | Leahy et al. |
| 6,287,295 B1 | 9/2001 | Chen et al. |
| 6,370,970 B1 | 4/2002 | Hosokawa et al. |
| 6,375,972 B1 | 4/2002 | Guo et al. |
| 6,390,791 B1 | 5/2002 | Maillefer et al. |

(56) References Cited

U.S. PATENT DOCUMENTS

| | | | |
|---|---|---|---|
| 6,408,878 B2 | 6/2002 | Unger et al. | |
| 6,413,238 B1 * | 7/2002 | Maget | A61M 5/14526 604/132 |
| 6,416,777 B1 | 7/2002 | Yaacobi | |
| 6,458,102 B1 | 10/2002 | Mann et al. | |
| 6,491,684 B1 | 12/2002 | Joshi et al. | |
| 6,520,936 B1 | 2/2003 | Mann | |
| 6,527,744 B1 | 3/2003 | Kriesel et al. | |
| 6,537,268 B1 | 3/2003 | Gibson et al. | |
| 6,589,205 B1 | 7/2003 | Meadows | |
| 6,669,950 B2 | 12/2003 | Yaacobi | |
| 6,697,694 B2 | 2/2004 | Mogensen | |
| 6,699,394 B2 | 3/2004 | Tai et al. | |
| 6,713,081 B2 | 3/2004 | Robinson et al. | |
| 6,719,750 B2 | 4/2004 | Varner et al. | |
| 6,817,252 B2 | 11/2004 | Wiklund et al. | |
| 6,852,097 B1 | 2/2005 | Fulton, III | |
| 6,852,106 B2 | 2/2005 | Watson et al. | |
| 6,899,137 B2 | 5/2005 | Unger et al. | |
| 6,948,918 B2 | 9/2005 | Hansen | |
| 6,955,670 B2 | 10/2005 | Martin et al. | |
| 6,973,718 B2 | 12/2005 | Sheppard, Jr. et al. | |
| 7,070,577 B1 | 7/2006 | Haller et al. | |
| 7,225,683 B2 | 6/2007 | Harnett et al. | |
| 7,276,050 B2 | 10/2007 | Franklin | |
| 7,351,303 B2 | 4/2008 | Liu et al. | |
| 7,429,258 B2 | 9/2008 | Angel et al. | |
| 7,470,267 B2 | 12/2008 | Joshi et al. | |
| 7,517,440 B2 | 4/2009 | Anex et al. | |
| 7,524,304 B2 | 4/2009 | Genosar | |
| 7,537,590 B2 | 5/2009 | Santini, Jr. et al. | |
| 7,544,190 B2 | 6/2009 | Pickup et al. | |
| 7,606,615 B2 | 10/2009 | Makower et al. | |
| 7,766,873 B2 | 8/2010 | Moberg et al. | |
| 7,828,771 B2 | 11/2010 | Chiang et al. | |
| 7,867,203 B2 | 1/2011 | Rosenberg et al. | |
| 7,887,508 B2 | 2/2011 | Meng et al. | |
| 7,931,643 B2 | 4/2011 | Olsen et al. | |
| 8,147,447 B2 | 4/2012 | Sundar et al. | |
| 8,231,609 B2 | 7/2012 | Pang et al. | |
| 8,285,328 B2 | 10/2012 | Caffey et al. | |
| 8,585,648 B2 | 11/2013 | Caffey | |
| 8,920,376 B2 | 12/2014 | Caffey et al. | |
| 8,939,930 B2 | 1/2015 | Li et al. | |
| 2002/0016569 A1 | 2/2002 | Critchlow et al. | |
| 2002/0026176 A1 | 2/2002 | Varner et al. | |
| 2002/0040208 A1 | 4/2002 | Flaherty et al. | |
| 2002/0103412 A1 | 8/2002 | Trimmer | |
| 2002/0156462 A1 | 10/2002 | Stultz | |
| 2002/0188282 A1 | 12/2002 | Greenberg | |
| 2003/0014014 A1 | 1/2003 | Nitzan | |
| 2003/0014036 A1 | 1/2003 | Varner et al. | |
| 2003/0064088 A1 | 4/2003 | Carvalho et al. | |
| 2003/0069560 A1 | 4/2003 | Adamis et al. | |
| 2003/0141618 A1 | 7/2003 | Braithwaite et al. | |
| 2004/0028655 A1 | 2/2004 | Nelson et al. | |
| 2004/0096410 A1 | 5/2004 | Maley et al. | |
| 2004/0100528 A1 | 5/2004 | Howkins et al. | |
| 2004/0106914 A1 | 6/2004 | Coppeta et al. | |
| 2004/0126253 A1 | 7/2004 | Gray et al. | |
| 2004/0143221 A1 | 7/2004 | Shadduck | |
| 2004/0175410 A1 | 9/2004 | Ashton et al. | |
| 2004/0188648 A1 | 9/2004 | Xie et al. | |
| 2004/0199130 A1 | 10/2004 | Chornenky et al. | |
| 2004/0208910 A1 | 10/2004 | Ashton et al. | |
| 2004/0228734 A1 | 11/2004 | Jeon et al. | |
| 2005/0010175 A1 | 1/2005 | Beedon et al. | |
| 2005/0065500 A1 | 3/2005 | Couvillon et al. | |
| 2005/0076242 A1 | 4/2005 | Breuer | |
| 2005/0096707 A1 | 5/2005 | Hill et al. | |
| 2005/0106225 A1 | 5/2005 | Massengale et al. | |
| 2005/0175708 A1 | 8/2005 | Carrasquillo et al. | |
| 2005/0187515 A1 | 8/2005 | Varrichio et al. | |
| 2005/0208103 A1 | 9/2005 | Adamis et al. | |
| 2005/0209562 A1 | 9/2005 | Kim | |
| 2005/0214129 A1 | 9/2005 | Greene et al. | |
| 2006/0004330 A1 * | 1/2006 | Carlisle | A61M 5/1408 604/246 |
| 2006/0012280 A1 | 1/2006 | Kang et al. | |
| 2006/0014793 A1 | 1/2006 | Nakamura et al. | |
| 2006/0047538 A1 | 3/2006 | Condurso et al. | |
| 2006/0052666 A1 | 3/2006 | Kumar et al. | |
| 2006/0052768 A1 | 3/2006 | Joshi et al. | |
| 2006/0075016 A1 | 4/2006 | Kanayama et al. | |
| 2006/0089619 A1 | 4/2006 | Ginggen | |
| 2006/0116641 A1 * | 6/2006 | Gordon | A61K 9/0004 604/141 |
| 2006/0167435 A1 | 7/2006 | Adamis et al. | |
| 2006/0178655 A1 | 8/2006 | Santini et al. | |
| 2006/0200073 A1 | 9/2006 | Radmer et al. | |
| 2006/0200097 A1 | 9/2006 | Humayun et al. | |
| 2006/0258994 A1 | 11/2006 | Avery | |
| 2006/0259015 A1 | 11/2006 | Steinbach | |
| 2006/0271020 A1 | 11/2006 | Huang et al. | |
| 2007/0021735 A1 | 1/2007 | Bhavaraju et al. | |
| 2007/0060870 A1 | 3/2007 | Tolle et al. | |
| 2007/0066939 A1 | 3/2007 | Krulevitch et al. | |
| 2007/0084765 A1 | 4/2007 | Tse | |
| 2007/0093752 A1 | 4/2007 | Zhao et al. | |
| 2007/0106199 A1 | 5/2007 | Krivoy et al. | |
| 2007/0106218 A1 | 5/2007 | Yodfat et al. | |
| 2007/0106557 A1 | 5/2007 | Varghese | |
| 2007/0112328 A1 | 5/2007 | Steinbach et al. | |
| 2007/0118066 A1 | 5/2007 | Pinchuk et al. | |
| 2007/0173900 A1 | 7/2007 | Siegel et al. | |
| 2007/0191770 A1 | 8/2007 | Moberg et al. | |
| 2007/0228071 A1 * | 10/2007 | Kamen | G05D 7/0647 222/52 |
| 2007/0255233 A1 | 11/2007 | Haase | |
| 2007/0255235 A1 | 11/2007 | Olsen et al. | |
| 2007/0255250 A1 | 11/2007 | Moberg et al. | |
| 2007/0255261 A1 | 11/2007 | Haase | |
| 2007/0269487 A1 | 11/2007 | de Juan et al. | |
| 2007/0275384 A1 | 11/2007 | Leppert et al. | |
| 2008/0015494 A1 | 1/2008 | Santini et al. | |
| 2008/0022789 A1 | 1/2008 | Okuno et al. | |
| 2008/0033255 A1 | 2/2008 | Essenpreis et al. | |
| 2008/0039768 A1 | 2/2008 | Francis | |
| 2008/0039792 A1 * | 2/2008 | Meng | A61K 9/0024 604/114 |
| 2008/0097412 A1 | 4/2008 | Shuros et al. | |
| 2008/0102119 A1 | 5/2008 | Grovender et al. | |
| 2008/0119707 A1 | 5/2008 | Stafford | |
| 2008/0125702 A1 | 5/2008 | Blischak et al. | |
| 2008/0170936 A1 | 7/2008 | Den Toonder et al. | |
| 2008/0181930 A1 | 7/2008 | Rodstrom et al. | |
| 2008/0194053 A1 | 8/2008 | Huang | |
| 2008/0234637 A1 | 9/2008 | McConnell et al. | |
| 2008/0243071 A1 | 10/2008 | Quijano et al. | |
| 2008/0269664 A1 | 10/2008 | Trovato et al. | |
| 2008/0269678 A1 * | 10/2008 | Rebours | A61M 5/16827 604/118 |
| 2008/0275384 A1 | 11/2008 | Mastrototaro | |
| 2008/0312584 A1 | 12/2008 | Montgomery et al. | |
| 2009/0028824 A1 * | 1/2009 | Chiang | A61M 5/14248 424/85.7 |
| 2009/0041624 A1 | 2/2009 | Hochmuth et al. | |
| 2009/0112188 A1 | 4/2009 | Santini, Jr. et al. | |
| 2009/0188576 A1 | 7/2009 | Kang et al. | |
| 2009/0192493 A1 | 7/2009 | Meng et al. | |
| 2009/0205399 A1 | 8/2009 | Sun et al. | |
| 2009/0227855 A1 | 9/2009 | Hill et al. | |
| 2009/0234366 A1 | 9/2009 | Tsai et al. | |
| 2009/0234594 A1 | 9/2009 | Carlisle et al. | |
| 2009/0240215 A1 | 9/2009 | Humayun et al. | |
| 2009/0259176 A1 | 10/2009 | Yairi | |
| 2009/0281528 A1 | 11/2009 | Grovender et al. | |
| 2009/0306585 A1 | 12/2009 | Pang et al. | |
| 2009/0306594 A1 | 12/2009 | Pang et al. | |
| 2009/0306595 A1 | 12/2009 | Shih et al. | |
| 2009/0306633 A1 | 12/2009 | Trovato et al. | |
| 2009/0308752 A1 | 12/2009 | Evans et al. | |
| 2009/0311133 A1 | 12/2009 | Pang et al. | |
| 2009/0312742 A1 | 12/2009 | Pang et al. | |

(56) References Cited

U.S. PATENT DOCUMENTS

| | | |
|---|---|---|
| 2010/0004639 A1 | 1/2010 | Pang et al. |
| 2010/0030550 A1 | 2/2010 | Travieso et al. |
| 2010/0049120 A1 | 2/2010 | Dijksman et al. |
| 2010/0101670 A1 | 4/2010 | Juncker et al. |
| 2010/0114002 A1 | 5/2010 | O'Mahony et al. |
| 2010/0143448 A1 | 6/2010 | Nisato et al. |
| 2010/0222769 A1 | 9/2010 | Meng et al. |
| 2010/0234805 A1 | 9/2010 | Kaufmann et al. |
| 2010/0241103 A1 | 9/2010 | Kraft et al. |
| 2010/0292557 A1* | 11/2010 | Pesach ............... A61B 5/14532 600/365 |
| 2010/0292635 A1 | 11/2010 | Sundar |
| 2010/0305550 A1 | 12/2010 | Meng et al. |
| 2011/0144586 A1 | 6/2011 | Michaud et al. |
| 2011/0184342 A1 | 7/2011 | Pesach et al. |
| 2011/0190702 A1 | 8/2011 | Stumber |
| 2011/0202032 A1 | 8/2011 | Shih et al. |
| 2011/0270188 A1 | 11/2011 | Caffey et al. |
| 2011/0275410 A1 | 11/2011 | Caffey et al. |
| 2011/0275987 A1 | 11/2011 | Caffey et al. |
| 2012/0041427 A1 | 2/2012 | Caffey et al. |
| 2012/0046651 A1 | 2/2012 | Beyer et al. |
| 2012/0222488 A1 | 9/2012 | Slocum |
| 2012/0283691 A1 | 11/2012 | Barnes et al. |
| 2013/0178792 A1 | 7/2013 | Li et al. |
| 2013/0178826 A1 | 7/2013 | Li et al. |
| 2013/0184640 A1 | 7/2013 | Li et al. |
| 2013/0184641 A1 | 7/2013 | Li |
| 2013/0276974 A1 | 10/2013 | Pang et al. |
| 2013/0289497 A1 | 10/2013 | Humayun et al. |
| 2013/0296810 A1 | 11/2013 | Humayun et al. |
| 2014/0074058 A1 | 3/2014 | Shih et al. |
| 2014/0088554 A1 | 3/2014 | Li et al. |
| 2014/0088555 A1 | 3/2014 | Li et al. |
| 2014/0094770 A1 | 4/2014 | Li et al. |

FOREIGN PATENT DOCUMENTS

| | | |
|---|---|---|
| CN | 103108665 A | 5/2013 |
| CN | 102202719 B | 11/2014 |
| CN | 104353150 A | 2/2015 |
| DE | 3915708 A1 | 2/1990 |
| DE | 4436540 A1 | 4/1996 |
| DE | 102004036358 A1 | 2/2006 |
| EP | 209677 A1 | 1/1987 |
| EP | 251680 A2 | 1/1988 |
| EP | 646381 A1 | 4/1995 |
| EP | 815896 A2 | 1/1998 |
| EP | 1649884 A1 | 4/2006 |
| EP | 1841491 A1 | 10/2007 |
| EP | 2467797 A1 | 6/2012 |
| EP | 2560703 A2 | 2/2013 |
| EP | 2780055 A2 | 9/2014 |
| EP | 2320989 B1 | 3/2015 |
| GB | 1345764 A | 2/1974 |
| GB | 1452104 A | 10/1976 |
| IE | 38474 B1 | 3/1978 |
| JP | 2003-299732 A | 10/2003 |
| JP | 2015-502785 A | 1/2015 |
| WO | 84/01718 A1 | 5/1984 |
| WO | 86/07269 A1 | 12/1986 |
| WO | 95/13838 A1 | 5/1995 |
| WO | 96/41159 A1 | 12/1996 |
| WO | 99/17749 A1 | 4/1999 |
| WO | 99/38552 A1 | 8/1999 |
| WO | 99/62576 A1 | 12/1999 |
| WO | 00/26367 A2 | 5/2000 |
| WO | 00/40089 A1 | 7/2000 |
| WO | 00/72900 A1 | 12/2000 |
| WO | 00/74751 A1 | 12/2000 |
| WO | 01/12158 A1 | 2/2001 |
| WO | 01/21234 A1 | 3/2001 |
| WO | 01/26706 A2 | 4/2001 |
| WO | 01/56634 A1 | 8/2001 |
| WO | 01/66173 A1 | 9/2001 |
| WO | 01/94784 A1 | 12/2001 |
| WO | 02/40083 A2 | 5/2002 |
| WO | 02/067688 A1 | 9/2002 |
| WO | 03/002170 A2 | 1/2003 |
| WO | 03/009774 A2 | 2/2003 |
| WO | 03/024360 A1 | 3/2003 |
| WO | 03/072193 A1 | 9/2003 |
| WO | 03/090509 A2 | 11/2003 |
| WO | 2004/002878 A2 | 1/2004 |
| WO | 2004/014969 A1 | 2/2004 |
| WO | 2004/026281 A2 | 4/2004 |
| WO | 2004/066871 A2 | 8/2004 |
| WO | 2004/067066 A1 | 8/2004 |
| WO | 2004/073551 A2 | 9/2004 |
| WO | 2005/034814 A1 | 4/2005 |
| WO | 2005/046769 A2 | 5/2005 |
| WO | 2006/012280 A1 | 2/2006 |
| WO | 2006/014793 A1 | 2/2006 |
| WO | 2006/026768 A1 | 3/2006 |
| WO | 2006/060586 A1 | 6/2006 |
| WO | 2006/075016 A1 | 7/2006 |
| WO | 2006/121921 A2 | 11/2006 |
| WO | 2007/035621 A1 | 3/2007 |
| WO | 2007/065944 A1 | 6/2007 |
| WO | 2007/084765 A2 | 7/2007 |
| WO | 2007/106557 A2 | 9/2007 |
| WO | 2007/112328 A2 | 10/2007 |
| WO | 2007/125456 A2 | 11/2007 |
| WO | 2007/138590 A2 | 12/2007 |
| WO | 2008/024808 A2 | 2/2008 |
| WO | 2008/054788 A2 | 5/2008 |
| WO | 2008/139460 A2 | 11/2008 |
| WO | 2008/151667 A1 | 12/2008 |
| WO | 2009/015389 A2 | 1/2009 |
| WO | 2009/048144 A1 | 4/2009 |
| WO | 2009/086112 A2 | 7/2009 |
| WO | 2009/137780 A2 | 11/2009 |
| WO | 2011/022484 A1 | 2/2011 |
| WO | 2011/025913 A1 | 3/2011 |
| WO | 2011/028997 A1 | 3/2011 |
| WO | 2011/133724 A2 | 10/2011 |
| WO | 2011/133724 A3 | 1/2012 |
| WO | 2013/075109 A2 | 5/2013 |
| WO | 2013/075109 A9 | 7/2013 |
| WO | 2013/075109 A3 | 10/2013 |
| WO | 2014/047638 A1 | 3/2014 |
| WO | 2014/047657 A2 | 3/2014 |
| WO | 2014/047657 A3 | 7/2014 |
| WO | 2015/048093 A2 | 4/2015 |

OTHER PUBLICATIONS

PCT International Patent Application No. PCT/US2013/061443, International Preliminary Report on Patentability issued Mar. 24, 2015, 9 pages.

PCT International Patent Application No. PCT/US2013/061494, International Preliminary Report on Patentability issued Mar. 24, 2015, 13 pages.

PCT International Patent Application No. PCT/US2014/057158, International Search Report and Written Opinion mailed Mar. 30, 2015, 14 pages.

Examination Report Received for European Patent Application No. 10760475.3, mailed on Apr. 7, 2015, 7 pages.

Examination Report in European Patent Application No. 07753177.0, mailed on Jan. 29, 2009, 6 pages.

Examination Report in European Patent Application No. 07753177.0, mailed on Feb. 5, 2010, 3 pages.

Extended Search Report issued for European Patent Application No. 11153615.7, mailed on Dec. 15, 2011, 8 pages.

Examination Report in European Patent Application No. 11153618.1, mailed on Oct. 14, 2013, 5 pages.

Extended Search Report issued for European Patent Application No. 11153618.1, mailed on Dec. 12, 2011, 9 pages.

Extended Search Report issued for European Patent Application No. 13168508.3, mailed on Oct. 24, 2013, 7 pages.

(56) References Cited

OTHER PUBLICATIONS

Office Action mailed on Apr. 9, 2013 for Japanese Patent Application No. 2010-539873, English translation of "Notification of Reason for Rejection", 6 pages.

Examination Report in Mexican Patent Application No. MX/a/2008/011714, mailed on Jan. 19, 2012.

Examination Report in Mexican Patent Application No. MX/A/2010/012213, mailed on Jan. 16, 2014.

International Application Serial No. PCT/US2007/006530, International Search Report and Written Opinion mailed on Nov. 12, 2007, 15 pages.

International Application Serial No. PCT/US2007/006530, Invitation to Pay Additional Fees and Partial International Search mailed on Jul. 31, 2007, 7 pages.

International Application Serial No. PCT/US2008/087690, International Search Report and Written Opinion mailed on Aug. 11, 2009, 15 pages.

International Application Serial No. PCT/US2008/087690, Invitation to Pay Additional Fees and Partial International Search mailed on May 15, 2009, 5 pages.

International Application Serial No. PCT/US2009/030019, International Search Report and Written Opinion mailed on Jul. 20, 2009, 16 pages.

International Application Serial No. PCT/US2009/030019, Invitation to Pay Additional Fees and Partial International Search mailed on Jun. 5, 2009, 5 pages.

International Application Serial No. PCT/US2009/043313, International Search Report and Written Opinion mailed on Feb. 25, 2010, 16 pages.

International Application Serial No. PCT/US2009/043313, Invitation to Pay Additional Fees and Partial International Search mailed on Nov. 16, 2009, 6 pages.

International Application Serial No. PCT/US2009/043317, International Search Report and Written Opinion mailed on Feb. 16, 2010, 15 pages.

International Application Serial No. PCT/US2009/043317, Invitation to Pay Additional Fees and Partial International Search, mailed on Nov. 16, 2009, 5 pages.

International Application Serial No. PCT/US2009/043325, International Search Report and Written Opinion mailed on Nov. 12, 2009, 18 pages.

International Application Serial No. PCT/US2010/045897, International Search Report and Written Opinion mailed on Dec. 28, 2010, 12 pages.

International Application Serial No. PCT/US2010/047811, Invitation to Pay Additional Fees and Partial Search Report mailed on Dec. 2, 2010, 8 pages.

International Application Serial No. PCT/US2011/033329, International Search Report and Written Opinion mailed Nov. 23, 2011, 16 pages.

International Application Serial No. PCT/US2011/033329, Invitation to Pay Additional Fees and Partial Search Report, mailed Aug. 4, 2011, 5 pages.

International Application Serial No. PCT/US2011/044508, International Search Report and Written Opinion mailed Dec. 1, 2011, 11 pages.

International Application Serial No. PCT/US2013/061494, Invitation to Pay Additional Fees and Partial Search Report, mailed Jan. 28, 2014, 6 pages.

"Krupin Eye Valve with Scleral Buckle, Krupin Eye Valve With Disk", Hood Laboratories Catalogue, F 079 Rev., Nov. 1992, 4 pages.

"The Optimed Advantage—Glaucoma Pressure Regulator", Optimed Advertising Brochure, Journal of Glaucoma, vol. 2, No. 3, 1993, 4 pages.

Chen et al., "Floating-Disk Parylene Micro Check Valve", Micro Electro Mechanical Systems, MEMS, IEEE 20th International Conference, Jan. 21-25, 2007, pp. 453-456.

Chen et al., "Floating-Disk Parylene Microvalve for Self-Regulating Biomedical Flow Controls", Micro Electro Mechanical Systems, MEMS, IEEE 21st International Conference., Jan. 13-17, 2008, pp. 575-578.

Chen et al., "Surface-Micromachined Parylene Dual Valves for On-Chip Unpowered Microflow Regulation", Journal of Microelectromechanical Systems, vol. 16, No. 2, Apr. 2007, pp. 223-231.

Choudhri et al., "A Comparison of Dorzolamide-Timolol Combination Versus the Concomitant Drugs", American Journal of Ophthalmology, vol. 130, No. 6, Dec. 2000, pp. 832-833.

Durham, N.C., "FDA Approves an Industry First!—The MED-EL Cochlear Implant System is FDA Approved for Use With Magnetic Resonance Imaging (MRI)", PR Newswire, Jun. 18, 2003, 3 pages.

Eliason et al., "An Ocular Perfusion System", Investigate Ophthalmology Visual Science, vol. 19, No. 1, Jan. 1980, pp. 102-105.

Hashizoe et al., "Scleral Plug of Biodegradable Polymers for Controlled Drug Release in the Vitreous", Arch Ophthalmology, vol. 112, No. 10, Oct. 1994, pp. 1380-1384.

Jabs, Douglas A., "Treatment of Cytomegalovirus Retinitis—1992", Arch Ophthalmology, vol. 110, No. 2, Feb. 1992, pp. 185-187.

Khouri et al., "Use of Fixed-Dose Combination Drugs for the Treatment of Glaucoma", Drugs & Aging, vol. 24, No. 12, Dec. 2007, pp. 1007-1016.

Kimura et al., "A New Vitreal Drug Delivery System Using an Implantable Biodegradable Polymeric Device", Investigative Ophthalmology & Visual Science, vol. 35, No. 6, May 1994, pp. 2815-2819.

Lo et al., "A Refillable Polymer Drug Delivery Device for Treatment of Ocular Diseases", The Royal Society of Chemistry, Jan. 1, 2007, 28 pages.

Michelson et al., "Experimental EndophtalmitisTreated With an Implantable Osmotic Minipump", Arch. Ophthalmology, vol. 97, Jul. 1979, pp. 1345-1346.

Miki et al., "A Method for Chronic Drug Infusion Into the Eye", Japanese Journal of Ophthalmology, vol. 28, No. 2, 1984, pp. 140-146.

Pincus et al., "Why are Only 50% of Courses of Anti-Tumor Necrosis Factor Agents Continued for Only 2 Years in Some Settings? Need for Longterm Observations in Standard Care to Compliment Clinical Trials", Journal of Reumatoloqy, vol. 33, No. 12, Dec. 2006, pp. 2372-2375.

Pope et al., "MRI in Patients with High-Grade Gliomas Treated with Bevacizumab and Chemotherapy", Neurology, vol. 66, No. 8, Apr. 2006, pp. 1258-1260.

Rubsamen et al., "Prevention of Experimental Proliferative Vitreoretinopathy With a Biodegradable Intravitreal Implant for the Sustained Release of Fluorouracil", Arch. Ophthalmology, vol. 112, No. 3, Mar. 1994, pp. 407-413.

Sanborn et al., "Sustained-Release Ganciclovir Therapy for Treatment of Cytomegalovirus Retinitis", Arch Ophthmology, vol. 110, No. 2, Feb. 1992, pp. 188-195.

Smith et al., "Intravitreal Sustained-Release Ganiclovir", Arch Ophthlmology, vol. 110, No. 2, Feb. 1992, pp. 255-258.

Stark-Vance, "Bevacizumab and CPT-11 in the Treatment of Relapsed Malignant Glioma", Neuro Oncology, vol. 7, No. 3, Abstract from the World Federation of Neuro-Oncology Second Quadrennial Meeting and Sixth Meeting of the European Association for Neuro-Oncology, May 5-8, 2005, Abstract 342, Jul. 2005, p. 369.

Steyer, Robert, "Alcon Eye-Drug Setback Raises the Stakes", Available online at <http://www.thestreet.com/story/10187873/1/alcon-eye-drug-setback-raises-the-stakes.html>, Oct. 14, 2004, 4 pages.

Strohmaier et al., "The Efficacy and Safety of the Dorzolamide-Timolol Combination Versus the Concomitant Administration of its Components", Ophthalmology, vol. 105, No. 10, Oct. 1998, pp. 1936-1944.

Xie et al., "An Electrochemical Pumping System for On-Chip Gradient Generation", Analytical Chemistry, vol. 76, No. 13, May 2004, pp. 3756-3763.

First Examiner Report received for Australian Application No. 2010284216 mailed Mar. 20, 2014, 5 pages.

(56) References Cited

OTHER PUBLICATIONS

Examiner Report received for Japanese Application No. 2011-508709 mailed Mar. 4, 2014, 5 pages (3 pages of English Translation and 2 pages of Office Action).

Examination Report received for Chinese Patent Application No. 200980126549.2 mailed Apr. 28, 2014, 3 pages.

Examination Report received for Chinese Patent Application No. 201080046911.8 mailed May 6, 2014, 8 pages.

Examination Report received for Chinese Patent Application No. 201180030341.8 mailed Jul. 2, 2014, 7 pages.

Examination Report received for Japanese Patent Application No. 2012-525667 mailed on Jun. 6, 2014, 9 pages (5 pages of English Translation and 4 pages).

Examination Report received for Mexican Patent Application No. MX/a/2010/012213 mailed Apr. 16, 2014.

Examination Report received for Mexican Patent Application No. MX/a/2013/013831 mailed on Mar. 26, 2014, 1 page.

International Application No. PCT/US2012/065874, International Preliminary Report on Patentability mailed May 30, 2014, 7 pages.

International Application No. PCT/US2012/065874, International Search Report and Written Opinion mailed Aug. 7, 2013, 13 pages.

International Application No. PCT/US2013/061443, International Search Report mailed on Jan. 21, 2014, 3 pages.

International Application No. PCT/US2013/061494, International Search Report and Written Opinion mailed May 28, 2014, 21 pages.

Notice of Allowance received for Chinese Patent Application No. 200980126549.2, mailed on Aug. 6, 2014, 4 pages (2 pages of original and 2 pages of English translation).

Examination Report Received for Chinese Patent Application No. 201080046911.8 mailed on Dec. 3, 2014, 6 pages (In accordance with 37 CFR § 1.98(a) (3)).

Examination Report Received for Mexican Patent Application No. MX/a/2012/002063 mailed on Feb. 27, 2015.

Examination Report Received for Mexican Patent Application No. MX/a/2010/012213 mailed on Jan. 5, 2015.

PCT International Patent Application No. PCT/US2010/045897, International Preliminary Report on Patentability mailed Mar. 1, 2012, 9 pages.

PCT International Patent Application No. PCT/US2011/033329, International Preliminary Report on Patentability mailed Nov. 1, 2012, 13 pages.

\* cited by examiner

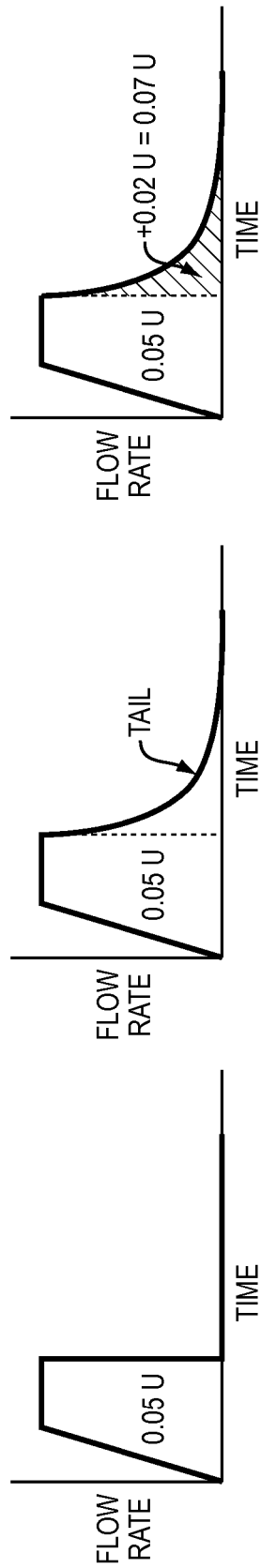
FIG. 4A
FIG. 4B
FIG. 4C
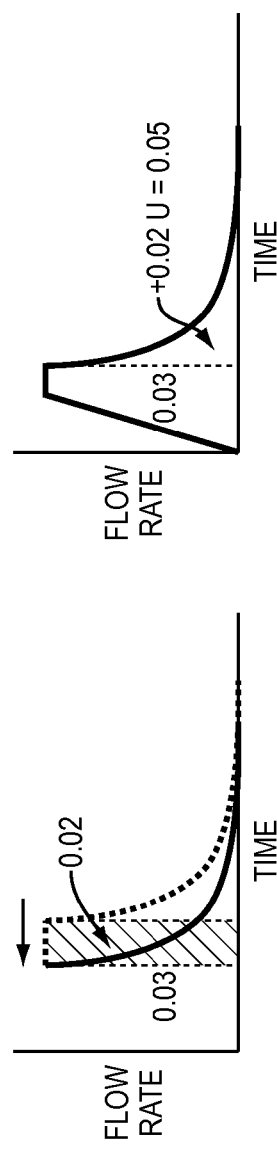
FIG. 4D
FIG. 4E

DRUG-DELIVERY PUMP WITH INTELLIGENT CONTROL

CROSS-REFERENCE TO RELATED APPLICATIONS

This is a continuation-in-part of U.S. Ser. No. 12/858,808, filed on Aug. 18, 2010, and also claims priority to, and the benefits of, U.S. Ser. No. 61/704,946, filed on Sep. 24, 2012; the entire disclosures of these applications are hereby incorporated by reference.

TECHNICAL FIELD

The present invention relates to drug-delivery devices, and in particular to control of piston- or plunger-driven drug-pump devices for accurate dosing.

BACKGROUND

Subcutaneous drug delivery is employed for treatment of conditions such as diabetes, and typically involves modalities such as syringe injections, pre-filled pen injectors and patient-filled portable insulin pumps. Pre-filled pen injectors provide accurate manual insulin dosing using, for example, a pre-filled, bubble-free glass cartridge. Since the glass cartridges are bubble-free, the priming process is simple for the patient. Since the injection is performed manually, however, patient compliance is a challenge; the patient may not observe proper injection timing and/or fail to follow the dosing prescription. Portable insulin pumps can provide fully controlled insulin delivery, improving patient compliance, and reduced numbers of injections (once every 3 days, for example) and programmable dosing schedules enhance the patient's quality of life. Patch pumps with low pump profiles can be attached to the patient's skin without interfering with daily activities such as including showering, sleeping, and exercising. Because these pumps are typically filled by patients, however, risks arise during the priming procedure. Improperly primed reservoirs may contain large air bubbles and cause the pump to inject too much air into the subcutaneous tissue, which poses serious safety concerns.

Accordingly, portable pumps with small footprints and pre-filled drug reservoirs can address various problems including those discussed above. One of the challenges for pumps utilizing glass vials as drug reservoirs is to provide controlled and accurate drug delivery. This challenge arises due to varying stiction/friction forces between the surface of the plunger and glass vial. Even under the same driving pressure, these variable forces may cause the drug to be delivered at different flow rates for basal (continuous) delivery. It will also make bolus delivery (i.e., delivery of a discrete dose over a short time period) unpredictable from one bolus to the next.

A related problem observed in connection with piston-driven pumps is a characteristic residual "tailing" of the flow rate—that is, if the amount of fluid expelled is plotted as a function of time, the plot will contain an asymmetric peak having a steepened front portion and an extended tail portion. This is evident, for example, in many drug-delivery devices that contain a drug reservoir formed of compliant materials. This tailing effect leads to a longer delivery time and, once again, inaccuracies in delivery volume.

SUMMARY

Embodiments of the present invention utilize a closed-loop feedback control system to ensure accurate drug delivery. This control system may, for example, utilize a flow sensor to measure the volume of delivery and an intelligent control algorithm to anticipate and compensate for overdoses and underdoses. Feedback control systems in accordance herewith can be applied to any piston- or plunger-driven pump system (hereafter, collectively, "driven" pumps) utilizing sensors that measure flow directly or indirectly. An advantage to this approach is adaptation of the control algorithm to the pump's output, ultimately resulting in extremely accurate drug delivery.

In general overview, a driven pump device in accordance herewith typically includes a cylindrical vial or cartridge with an outlet, and a piston or plunger movable therein. The piston/plunger divides the interior of the vial into a front chamber that is filled with liquid drug and, thus, forms the drug reservoir, and a back chamber that contains the pump mechanism that drives the piston. For example, in electrolytic drug pump devices, the back chamber, or "pump chamber," may contain a pair of electrodes and an electrolyte from which, upon application of a drive current to the electrodes, electrolysis gas evolves, building up pressure in the chamber that pushes the piston forward so as to expel drug through the outlet. Other pump mechanisms (e.g., osmotic, electrochemical, motor-driven, etc.) may also be used.

In general, the drug flow rate of a piston pump device can be regulated via the drive force/pressure applied by the pump; for electrolytically driven pump devices, for example, this is, in turn, a function of the drive current. The pump can be operated continuously to dispense drug at a desired steady flow rate, or in a "pulsed" manner (i.e., turning the pump on and off at certain intervals for specific periods of time) to deliver a series of discrete drug volumes. (Which mode of operation is used often depends on the drug regimen. For instance, diabetes patients usually need a continuous, low "basal" rate of insulin, in addition to high-rate, short-duration "bolus" deliveries before or after meals.) Sometimes, frequent small-volume bolus injections are used to provide, on average, a very low basal rate; this is called "discrete basal delivery." As explained above, the actual mechanics of piston pump devices can undermine the accuracy of drug delivery. One problem is the variable stiction/friction between the piston and glass vial, which can cause unstable flow rates despite constant drive pressure. Another problem is the compression of the piston (which is usually made of a rubber-like material) during pump operation, which results, after the pump has been turned off, in a residual "tail" of drug flow as the piston relaxes from its compressed state. This tail can be strongly affected, in addition, by fluid viscosity, which can vary with the particular drug composition as well as the temperature at administration. As a result of this tail, the actual drug volume delivered is larger than the "set" volume, which is the set flow rate during pump operation multiplied by the time period of operation Embodiments of the present invention address these inaccuracies by measuring the flow rate of drug (with any suitable flow-rate sensor disposed at the drug reservoir outlet or in a cannula, needle, or other fluid conduct downstream thereof) and adjusting pump operation based thereon in real time. For bolus deliveries, the "tail volume" (i.e., the volume of liquid delivered during the residual tail described above) may be measured during a priming stage (before drug is injected into the patient), and the "set volume" decreased such that the sum of tail volume and set volume equals the desired dosage. Similarly, for discrete basal delivery, the set volume for each pulse is adjusted based on the average tail volume of a number of immediately preceding pulses. For "continuous basal delivery" (or simply "continuous delivery"), in which fluid is dispensed continuously rather than in discrete pulses, the accumulated delivered volume may be repeatedly measured for a time window, and deviations of the measured volume from the target volume (i.e., the target flow rate times the length of the time window) are compensated for by adjusting the set flow rate for the next time window (typically between upper and lower flow-rate boundaries).

Accordingly, in a first aspect, the invention relates to a drug pump device. In various embodiments, the device comprises a drug reservoir; an exit member for fluidically connecting the reservoir with a drug injection site; a sensor; an electrolysis pump comprising a pump chamber in mechanical communication with the drug reservoir via an intervening displacement member, where the electrolysis pump is operable to exert a pressure to drive the displacement member toward the exit member and thereby force therethrough fluid in the drug chamber; and control circuitry for (i) storing a target delivered volume over a specified time, (ii) operating the electrolysis pump to force fluid from the drug reservoir into the exit member in pulses having a time window defined by a pump-start time when pumping begins and a pump-stop time when the pump is shut off, the time window corresponding to the target delivered volume at a predetermined flow rate, (iii) based on signals received from the sensor, measuring a volume of fluid through the exit member resulting from a pulse, the measured volume including a pulse volume through the exit member during the pulse and an additional tail volume through the exit member after the pulse, and (iv) adjusting the pulse time window based on the measured pulse volume and tail volume to conform collectively to the target delivered volume. In various embodiments, the sensor is at least one pressure sensor. In other embodiments, the sensor is at least one flow sensor, and in still other embodiments the sensor comprises or consists of at least one flow sensor and at least one pressure sensor.

The target delivered volume may correspond to a single bolus, in which case the control circuitry may cause measuring to occur during a priming stage and causing adjustment to occur during a delivery stage. Alternatively, the control circuitry may be configured to cause the target delivered volume to be dispensed through the exit member over a sequence of time-separated pulses occurring over a time interval; in these implementations, the control circuitry causes measuring to occur during a first time interval and causing adjustment to occur during a second time interval following the first time interval. In some embodiments, adjustment is based on the measured pulse volume and tail volume from a plurality of pulses.

In another aspect, the invention relates to a method of controlling an actual delivery volume of fluid to conform to a target delivery volume in a drug pump device comprising a drug reservoir, an exit member for fluidically connecting the reservoir with a drug injection site, and an electrolysis pump operable to force fluid from the drug reservoir into the exit member in pulses each having a time window defined by a pump-start time when pumping begins and a pump-stop time when the pump is shut off. The time window corresponds to a target delivered volume at a predetermined flow rate. In various embodiments, the method comprises measuring a volume of fluid through the exit member resulting from a pulse, where the measured volume includes (i) a pulse volume through the exit member during the pulse and (ii) an additional tail volume through the exit member after the pulse; and adjusting the pulse time window based on the measured pulse volume and tail volume to conform collectively to the target delivered volume. The measurement may be made with at least one pressure sensor and/or at least one flow sensor. In some embodiments the target delivered volume corresponds to a single bolus, in which case the measuring step occurs during a priming stage and the adjusting step occurs during a delivery stage. In other embodiments the target delivered volume is dispensed through the exit member over a sequence of time-separated pulses occurring over a time interval, in which case the measuring step occurs during a first time interval and the adjusting step occurs during a second time interval following the first time interval. Moreover, the adjusting step may be based on the measured pulse volume and tail volume from a plurality of pulses.

These and other objects, along with advantages and features of the present invention herein disclosed, will become more apparent through reference to the following description, the accompanying drawings, and the claims. Furthermore, it is to be understood that the features of the various embodiments described herein are not mutually exclusive and can exist in various combinations and permutations. As used herein, the term "substantially" means±10% and, in some embodiments, ±5%. A "measure" or "measurement" may be direct or indirect, i.e., a value derived from a directly measured value.

DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which:

FIGS. 4A-4E graphically depict operation of an adaptive control algorithm for overcoming a flow "tail";

DETAILED DESCRIPTION

1. Pump Architecture

Figure 1:
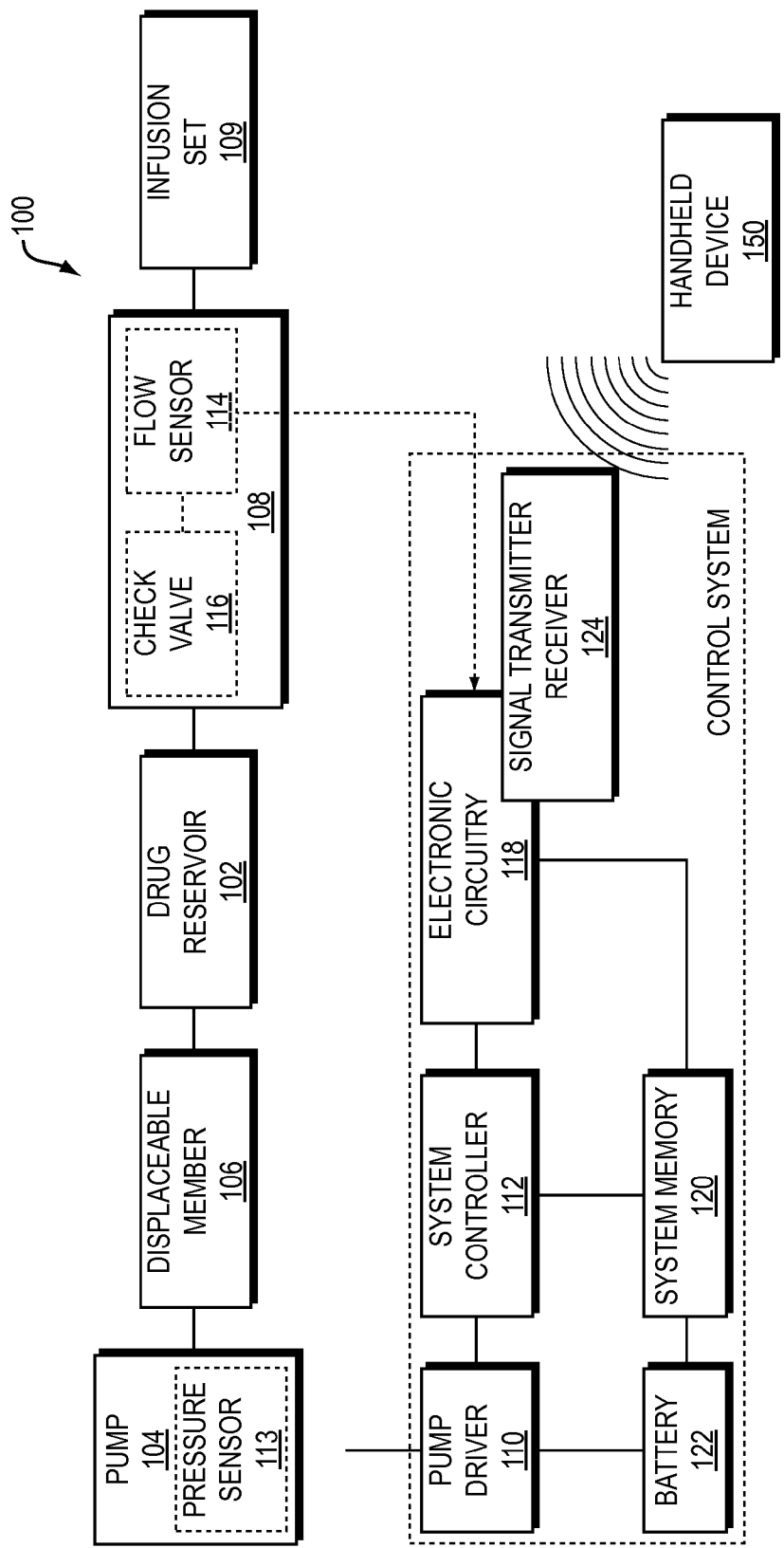
FIG. 1 is a block diagram illustrating the various functional components of electrolytic drug pump devices in accordance with various embodiments.

FIG. 1 illustrates, in block diagram form, the main functional components of a drug pump device 100 in accordance with various embodiments of the present invention. In general, the pump device 100 includes a drug reservoir 102 that interfaces with an electrolysis pump 104 via a displaceable member 106. The displaceable member 106 may be, for example, a piston, diaphragm, bladder, or plunger. In use, the drug reservoir 102 is filled with medication in liquid form, and pressure generated by the pump 104 moves or expands the displaceable member 106 so as to push the liquid drug out of the reservoir 102. A cannula, needle, or other exit member 108 connected to an outlet of the drug reservoir 102 conducts the liquid to an infusion set 109. The infusion set 109 may include a catheter fluidically connected to the cannula 108 for delivering the drug to a subcutaneous tissue region. A lancet and associated insertion mechanism may be used to drive the catheter through the skin. Alternatively, the infusion set 109 may include another type of drug-delivery vehicle, e.g., a sponge or other means facilitating drug absorption through the skin surface.

The electrolysis pump 104 generally includes an electrolyte-containing chamber (hereinafter also referred to as the "pump chamber") and, disposed in the chamber, one or more pairs of electrodes that are driven by a direct-current power source to break the electrolyte into gaseous products. Suitable electrolytes include water and aqueous solutions of salts, acids, or alkali, as well as non-aqueous ionic solutions. The electrolysis of water is summarized in the following chemical reactions:

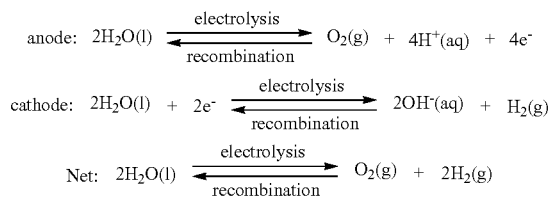

The net result of these reactions is the production of oxygen and hydrogen gas, which causes an overall volume expansion of the drug chamber contents. Gas evolution occurs even in a pressurized environment (reportedly at pressures of up to 200 MPa, corresponding to about 30,000 psi). As an alternative (or in addition) to water, ethanol may be used as an electrolyte, resulting in the evolution of carbon dioxide and hydrogen gas. Ethanol electrolysis is advantageous due to its greater efficiency and, consequently, lower power consumption, compared with water electrolysis. Electrolysis pumps in accordance with several embodiments are described in detail further below.

The pressure generated by the drug pump 104 may be regulated via a pump driver 110 by a system controller 112 (e.g., a microcontroller). The controller 112 may set the drive current and thereby control the rate of electrolysis, which, in turn, determines the pressure. In particular, the amount of gas generated is proportional to the drive current integrated over time, and can be calculated using Faraday's law of electrolysis. For example, creating two hydrogen and one oxygen molecule from water requires four electrons; thus, the amount (measured in moles) of gas generated by electrolysis of water equals the total electrical charge (i.e., current times time), multiplied by a factor of ¾ (because three molecules are generated per four electrons), divided by Faraday's constant.

The system controller 112 may execute a drug-delivery protocol programmed into the drug pump device 100, and may be responsive to one or more sensors 113, 114 that measure an operational parameter of the device 100, such as the pressure in the pump chamber 104 or the flow rate through (or pressure in) the cannula 108. For example, the controller 112 may adjust the current supplied to the electrolysis electrodes based on the pressure inside the pump chamber to achieve a target pressure. The target pressure, in turn, may be calculated based on a desired flow rate, using a known relationship between flow rate and pressure (as determined, e.g., by calibration). Due to the low cost of pressure sensors (such as, e.g., MEMS sensors as used in the automotive industry), this option is particularly advantageous for pumps designed for quick drug delivery. Indeed, two or more pressure sensors 113 may be placed in the pump chamber to simultaneously monitor pressure therein; this redundancy provides additional feedback to the controller 112, improves accuracy of information, and serves as a backup in case of malfunction of one of the sensors. Alternatively, the rate of drug flow out of the reservoir 102 may be measured directly and in real-time, using a flow sensor 114 integrated in the exit member 108 in a conventional manner. The total delivered dose can be computed by integrating the flow rate over time, and may serve as a control parameter for the electrolysis current as described in greater detail below.

In some embodiments, a pressure sensor 113 inside the pump chamber is used in combination with a flow sensor 114 in the cannula to increase the accuracy and precision of the feedback control loop. The use of multiple sensors also ensures that, in case the flow sensor 114 fails, the pressure sensor 113 would be able to detect high drug delivery rates, and shut the pump 104 down to avoid administration of an overdose to the patient or damage to the pump device. Conversely, the combination of flow and pressure sensors 114, 113 can also detect a violation in the drug reservoir 102 if pressure is measured in the pump chamber but no flow is measured in the cannula 108, indicating a potential leak. In general, the sensors used to measure various pump parameters may be flow, thermal, time of flight, pressure, or other sensors known in the art, and may be fabricated (at least in part) from parylene—a biocompatible, thin-film polymer. The cannula 108 may also include a check valve 116 that prevents accidental drug delivery and backflow of liquid into the drug reservoir 112; like the sensor 114, the check valve 116 may be made of parylene. In other embodiments, silicon or glass are used in part for the flow sensor 114 and valve 116 construction.

The drug pump device 100 may include electronic circuitry 118 (which may, but need not, be integrated with the system controller 112) for conditioning and further processing the sensor signal(s) and, optionally, providing pump status information to a user by means of LEDs, other visual displays, vibrational signals, or audio signals. In addition to controlling the drug pump 104, the controller 112 may be used to control other components of the drug pump system; for example, it may trigger insertion of the lancet and catheter. The system controller 112 may be a microcontroller, i.e., an integrated circuit including a processor core, memory (e.g., in the form of flash memory, read-only memory (ROM), and/or random-access memory (RAM)), and input/output ports. The memory may store firmware that directs operation of the drug pump device. In addition, the device may include read-write system memory 120. In certain alternative embodiments, the system controller 112 is a general-purpose microprocessor that communicates with the system memory 120. The system memory 120 (or memory that is part of a microcontroller) may store a drug-delivery protocol in the form of instructions executable by the controller 112, which may be loaded into the memory at the time of manufacturing, or at a later time by data transfer from a hard drive, flash drive, or other storage device, e.g., via a USB, Ethernet, or firewire port. In alternative embodiments, the system controller 112 comprises analog circuitry designed to perform the intended function.

The pump driver 110, system controller 112, and electronic circuitry 118 may be powered, via suitable battery electronics, by a battery 122. Suitable batteries 122 include non-rechargeable lithium batteries approximating the size of batteries used in wristwatches, as well as rechargeable Li-ion, lithium polymer, thin-film (e.g., Li-PON), nickel-metal-hydride, and nickel cadmium batteries. Other devices for powering the drug pump device 100, such as a capacitor, solar cell or motion-generated energy systems, may be used either in place of the battery 122 or supplementing a smaller battery. This can be useful in cases where the patient needs to keep the drug-delivery device 100 on for several days or more.

In certain embodiments, the drug pump device 100 includes, as part of the electronic circuitry 118 or as a separate component, a signal receiver 124 (for uni-directional telemetry) or a transmitter/receiver 124 (for bi-directional telemetry) that allows the device to be controlled and/or re-programmed remotely by a wireless handheld device 150, such as a customized remote control or a smartphone. In certain embodiments, the handheld device 150 and pump device 100 communicate over a (uni- or bidirectional) infrared (IR) link, which may utilize one or more inexpensive IR light-emitting diodes and phototransistors as transmitters and receivers, respectively. Communication between the drug pump device 100 and the handheld device 150 may also occur at radio frequencies (RF), using, e.g., a copper coil antenna as the transmitter/receiver component 124.

The drug-delivery device 100 may be manually activated, e.g., toggled on and off, by means of a switch integrated into the pump housing. In some embodiments, using the toggle switch or another mechanical release mechanism, the patient may cause a needle to pierce the enclosure of the drug reservoir 102 (e.g., the septum of a drug vial, as explained below with respect to FIGS. 2A and 2B) to establish a fluidic connection between the reservoir 102 and the cannula 108; priming of the pump can then begin. During priming, liquid is pumped from the reservoir through the fluid path, ideally displacing air with liquid up to the tip of the injection needle. Coupling insertion of the needle into the reservoir 102 with the activation of the pump device ensures the integrity of the reservoir 102, and thus protects the drug, up to the time when the drug is injected; this is particularly important for pre-filled drug pump devices. Similarly, the lancet and catheter of the infusion set 109 may be inserted by manually releasing a mechanical insertion mechanism. In some embodiments, insertion of the lancet and catheter automatically triggers electronic activation of a pump, e.g., by closing an electronic circuit. Alternatively, the pump and/or insertion set may be activated remotely by wireless commands.

The functional components of drug pump devices as described above may be packaged and configured in various ways. In certain preferred embodiments, the drug pump device is integrated into a patch adherable to the patient's skin. Suitable adhesive patches are generally fabricated from a flexible material that conforms to the contours of the patient's body and attaches via an adhesive on the backside surface that contacts a patient's skin. The adhesive may be any material suitable and safe for application to and removal from human skin. Many versions of such adhesives are known in the art, although utilizing an adhesive with gel-like properties may afford a patient particularly advantageous comfort and flexibility. The adhesive may be covered with a removable layer to preclude premature adhesion prior to the intended application. As with commonly available bandages, the removable layer preferably does not reduce the adhesion properties of the adhesive when removed. In some embodiments, the drug pump device is of a shape and size suitable for implantation.

The various components of the drug pump device may be held within a housing mounted on the skin patch. The device may either be fully self-contained, or, if implemented as discrete, intercommunicating modules, reside within a spatial envelope that is wholly within (i.e., which does not extend beyond in any direction) the perimeter of the patch. The housing may provide mechanical integrity and protection of the components of the drug pump device 100, and prevent disruption of the pump's operation from changes in the external environment (such as pressure changes). The control system components 110, 112, 118, 120, 122 may be mounted on a circuit board, which may be flexible and/or may be an integral part of the pump housing. In some embodiments, the control system components are integrated with the electrolysis electrodes into self-contained unit.

Drug pump devices 100 in accordance herewith may be designed for single or repeated use. Multi-use pumps generally include a one-way check valve and a flow sensor, as described above, in the cannula. Further, the drug reservoir of a multi-use pump may be refillable via a refill port, using, e.g., a standard syringe. In some embodiments, the drug pump device 100 is removed from the patient's skin for re-filling. The patient may, for example, place the drug pump device 100 and cartridge containing the new drug into a home refill system, where the pump device and cartridge may be aligned using, e.g., a press-machine mechanism. The patient may then press a button to trigger automatic insertion of a needle that draws liquid drug from the cartridge to the cannula in order to activate the electronics and begin priming the pump.

The electrolysis pump 104 and drug reservoir 102 may be arranged within the device 100 in different ways, the two most common being a piston-pump configuration, in which the pump chamber and reservoir are formed within an elongated vial and separated by a piston movable along the axis of the vial, and the diaphragm-pump configuration, in which the reservoir is disposed on top of the pump chamber and separated therefrom by a flexible diaphragm. Both configurations are described in detail in U.S. patent application Ser. No. 13/091,047, filed on Apr. 20, 2011, which is hereby incorporated herein by reference in its entirety.

Figure 2A:
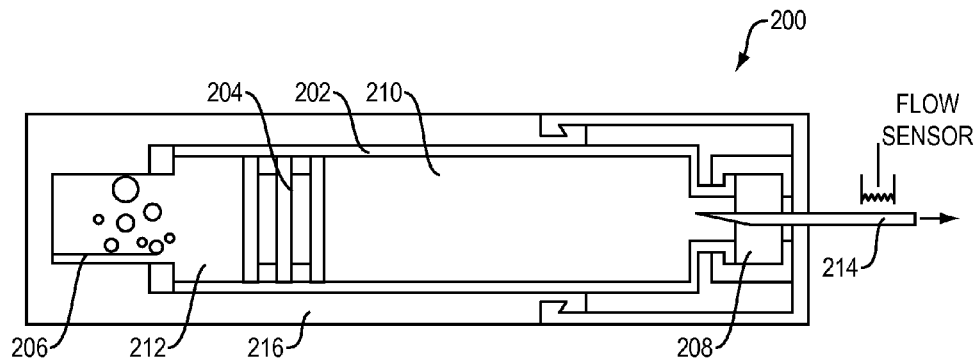
FIGS. 2A and 2B are schematic side views of piston pump devices in accordance with various embodiments.

FIG. 2A schematically illustrates an exemplary piston pump device 200. The pump device 200 includes a cylindrical (or, more generally, tubular) vial 202 with a piston 204 movably positioned therein and an electrolysis electrode structure 206 mounted to one end. A septum 208 may be disposed at the other end to seal the vial 202. Both the piston 204 and the septum 208 may be made of an elastomeric polymer material, such as a synthetic or natural rubber; in some embodiments, silicone rubber (i.e., polydiorganosiloxane, e.g., polydimethylsiloxane) is used. The piston 204 separates the interior of the vial 202 into a drug reservoir 210 and a pump chamber 212. In use, a needle 214 pierces the septum 208 to allow fluid egress from the drug reservoir 210; a cannula (not shown) connected to the needle 214 may conduct the fluid to the infusion set (not shown). The piston pump device 200 is enclosed in a protective housing 216, e.g., made of a hard plastic.

The electrodes 206 may be made of any suitable metal, such as, for example, platinum, titanium, gold, or copper, and may form a pair of parallel wires or plates. Alternatively, to improve electrolysis efficiency, the electrodes can have non-traditional shapes. For example, they may be interdigitated, or individually wound up into a spiral configuration (and oriented so as to face each other). Further, the electrodes 206 may be embedded in a hydrophilic absorbent material (e.g., a cotton ball) that ensures continuous contact with the electrolyte. This solves a problem frequently encountered with conventional electrolysis pumps, in which the electrodes are simply submerged in liquid electrolyte: as gaseous electrolysis products are generated, they push the piston towards the outlet end of the drug reservoir, thereby increasing the volume of the electrolysis chamber, which causes a decrease in the level of the electrolyte. Depending on the orientation of the device, one or both electrodes may, as a result, gradually emerge from the electrolyte and become surrounded by the gas, eventually forming an open circuit and, thus, causing the electrolysis reaction to cease. This problem can be avoided in various ways, one of which is to surround the electrodes with a hydrophilic absorbent material such as (but not limited to) a hydrogel, cotton ball, sponge, or super-absorbent polymer. The electrolyte stays inside the hydrophilic absorbent material, which efficiently expels the generated gas and keeps the electrodes replenished with electrolyte.

The vial 202 may be fabricated from a glass, polymer, or other materials that are inert with respect to the stability of the drug and, preferably, biocompatible. Polymer vials, e.g., made of polypropylene or parylene, may be suitable for certain drugs that degrade faster when in contact with glass, such as protein drugs. For many other drugs, glass is the preferred material. Glass is commonly used in commercially available and FDA-approved drug vials and containers from many different manufacturers. As a result, there are well-established and approved procedures for aseptically filling and storing drugs in glass containers, which may accelerate the approval process for drug pump devices that protect the drug in a glass container, and avoid the need to rebuild a costly aseptic filling manufacturing line. Using glass for the reservoir further allows the drug to be in contact with similar materials during shipping. Suitable glass materials for the vial may be selected based on the chemical resistance and stability as well as the shatterproof properties of the material. For example, to reduce the risk of container breakage, type-II or type-III soda-lime glasses or type-I borosilicate materials may be used.

To enhance chemical resistance and maintain the stability of enclosed drug preparations, the interior surface of the vial may have a specialized coating. Examples of such coatings include chemically bonded, invisible, ultrathin layers of silicon dioxide or medical-grade silicone emulsions. In addition to protecting the chemical integrity of the enclosed drugs, coatings such as silicone emulsions may provide for lower and more uniform friction between the piston and vial.

In certain embodiments, the piston pump device 200 is manufactured by fitting a conventional, commercially available glass or polymer drug vial, which may already be validated for aseptic filling, with the piston 204 and electrolysis pump components. A screw-in needle cassette may be placed over the septum 208, and a mechanical actuation mechanism may serve to screw the cassette into the vial 202 such that the cassette needle 214 punctures the septum 208 and establishes a connection with the cannula at the time the patient desires to use the pump. To accommodate the electrolysis pump, the vial 202 is, in some embodiments, longer than typical commercially available vials, but maintains all other properties such that validated filling methods and the parameters of existing aseptic filling lines need not be changed. The drug pump device may be furnished with a prefilled vial. If a glass vial is used, the drugs can be stored in the pump device for long-term shelf life without the need to change the labeling on the drug.

Figure 2B:
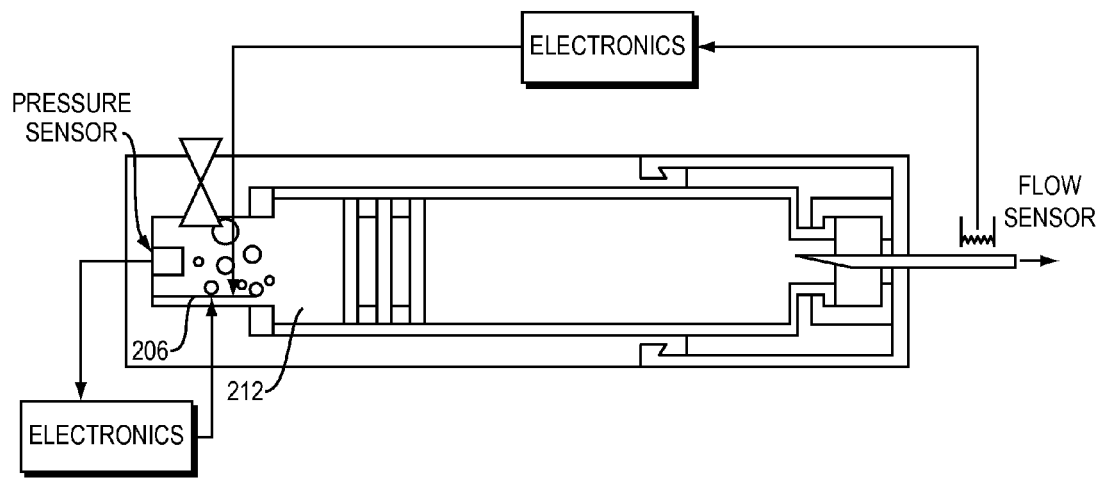

FIG. 2B illustrates the pump 200 with a pressure sensor located in the pump chamber 212. Signals from the flow sensor and the pressure sensor are received by programmable circuitry and may be used to regulate pump operation as described in detail below.

2. Feedback Control

Figure 3:
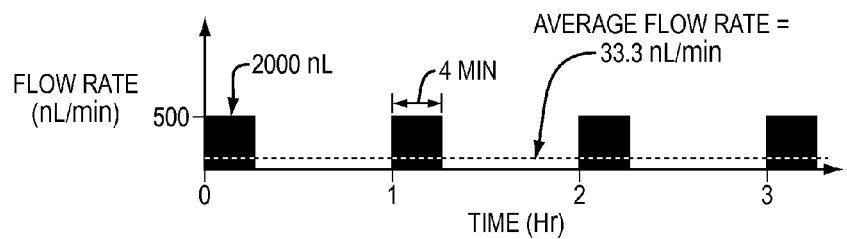
FIG. 3 illustrates how repeated, alternating pulses and non-delivery periods can be combined to obtain an averaged flow rate equal to a targeted flow.

Closed-loop feedback control in accordance herewith ensures accurate drug delivery in driven pumps. In one delivery scheme, a pump system delivers drug in discrete doses or pulses, resulting in flow rates that are much lower than the continuous delivery capabilities of the pump. Due to the effect of the stiction of the plunger and glass wall of the cartridge at such a low flow rate, each small discrete dose of drug is generated after the plunger is pushed to overcome the stiction force. Each discrete delivery may overshoot to a flow rate higher than a targeted flow rate, followed by an abrupt stop of the plunger movement causing the flow rate to cease for certain interval. Combining these repeated, alternating pulses and non-delivery periods results in an averaged flow rate theoretically equal to the targeted flow rate and the amount of dose volume equal to the volume obtained from continuous delivery mode. This approach is illustrated in FIG. 3, which shows a discrete dose mode in which the peak flow rate for each pulse is 500 nL/min, the duration for each pulse is 4 min, and the average flow rate representing a continuous constant delivery mode is 33.3 nL/min.

The mechanics of actually delivering these discrete doses, however, can result in inaccuracy (such as an overdose or underdose relative to the desired target delivery). When electrolysis occurs in an electrolytically driven plunger pump, pressure builds up behind the plunger, causing it to compress. When electrolysis stops, however, the plunger relaxes from this compressed state. The relaxation of the plunger material continues to push fluid out of the drug reservoir, causing a prolonged "tail" of the flow rate. This residual flow eventually ceases after the plunger returns to its natural state. The flow sensor enables the system to determine the actual dose delivered, triggering a control algorithm (such as an artificial neural network, fuzzy logic, etc.) that accounts for deviations from the target dose. In other embodiments, a pressure sensor in the pump chamber is used instead of, or in addition to, the flow sensor, since pressure readings are readily correlated with the volume of fluid expelled from the reservoir.

FIGS. 4A-4E illustrate the general concept of an adaptive control algorithm suitable for addressing this problem. In particular, FIG. 4A shows an ideal discrete dose of 0.05 U (which deviates from a perfectly rectangular pulse due to a necessary ramp-up time, which represents proper pump operation and does not vary significantly); FIG. 4B shows the actual delivered dose with additional volume "tail"; FIG. 4C illustrates measurement of the tail at 0.02 U, which totals 0.07 U delivered; the pump stops delivery early at 0.03 U, which accounts for the unwanted tail of 0.02 U shown in FIG. 4D (i.e., the pulse is adjusted so that the tail volume becomes part of the intended delivery volume rather than a deviation therefrom); and FIG. 4E illustrates performance in accordance with embodiments of the present invention, which results in a delivered dose that more accurately tracks the target dose shown in FIG. 4A.

A typical insulin pump should be able to provide bolus and background basal delivery rates over a wide range in order to serve different patients' needs. A prefilled insulin pump in accordance herewith can successfully provide suitable basal and bolus ranges. However, due to the nature of prefilled cartridge pumps, in particular the varying friction between the rubber plunger and glass wall among different cartridges, delivery accuracies can be compromised if corrections for such variation are not made. Thus, a real-time intelligent control algorithm may be used to compensate for the variation and maintain a very accurate dosage for both basal and bolus delivery.

Due to the unpredictable interaction between the plunger and glass cartridge of a driven pump, many variables can contribute to dosing inaccuracies. Since an initial stiction (initial static friction) exists between the plunger and glass vial, the pump must achieve a minimum pressure before the plunger can move smoothly to deliver a truly continuous flow rate. In this situation, only dynamic friction occurs between plunger and the glass container. On the other hand, the initial stiction (or static friction) may limit the minimum flow rate that the pump can offer and make it very difficult to deliver small amount of drug. To deliver at flow rates below this threshold, a discrete delivery scheme herein termed "discrete basal delivery" may be utilized. In this scheme, the target flow rate is converted to a target volume delivery in a given time period. Several small pulses of insulin are delivered throughout the given time span to achieve the target volume delivery, which fulfills the targeted average flow rate as described in the following equation.

$$\text{Flow Rate}\left(\frac{U}{Hr}\right) = \frac{\text{Total Delivery Volume }(U)}{\text{Time }(Hr)} \quad (3)$$

In one representative embodiment, the the volume of the tail is measured from the previous few (e.g., three) doses the average is determined. The system controller 112 then adjusts the target volume for the next dose based on this average. The following equations may be used by the controller to determine the proper correction.

$$V_{Tail\_Avg} = \frac{\sum_{k=0}^{n} V_{Tail}(k)}{n} \quad (1)$$

$$V_{set}(n) = V_{target}(n) - V_{Tail\_Avg} \quad (2)$$

where $V_{Tail\_Avg}$ is the average tail volume, $V_{Tail}$ is the individual tail volume, $V_{set}$ is the predicted volume to be delivered excluding the tail volume, and $V_{target}$ is the the total expected volume.

A similar approach may be used for continuous delivery. In particular, after analyzing the pump's previous average delivery during a given time period, the system controller 112 adjusts the overall flow rate (on a pulse-by-pulse basis) to correct for the previous delivery error during the next time period.

Figure 5:
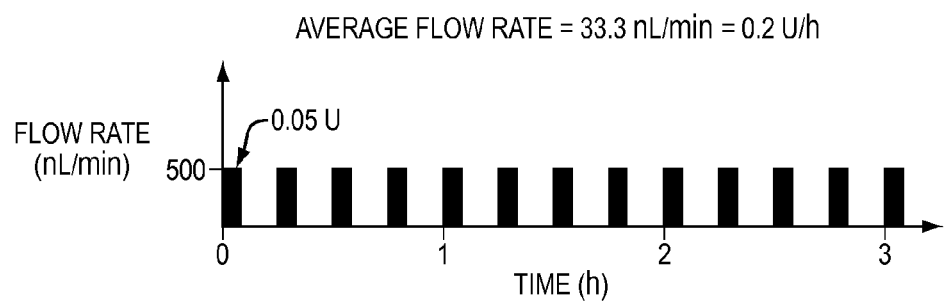
FIG. 5, like FIG. 3, illustrates an example of discrete basal delivery achieved by multiple pulse/time deliveries.

FIG. 5 illustrates an example of discrete basal delivery achieved by multiple pulse/time deliveries. As shown, there are four bolus deliveries in an hour and the equivalent flow rate is 33.3 nL/min. To generate these small pulses, the pressure in the electrolysis chamber is quickly released at the end of each pulse to accurately obtain the targeted volume for each small pulse. If the pressure is not promptly released, the high pressure will prevent the pump flow from stopping and result in a large over-delivery. Meanwhile, due to residual pressure induced from the plunger/glass interaction and the compliance of the plunger, a "tail" is produced that degrades the accuracy of basal delivery.

Figure 6:
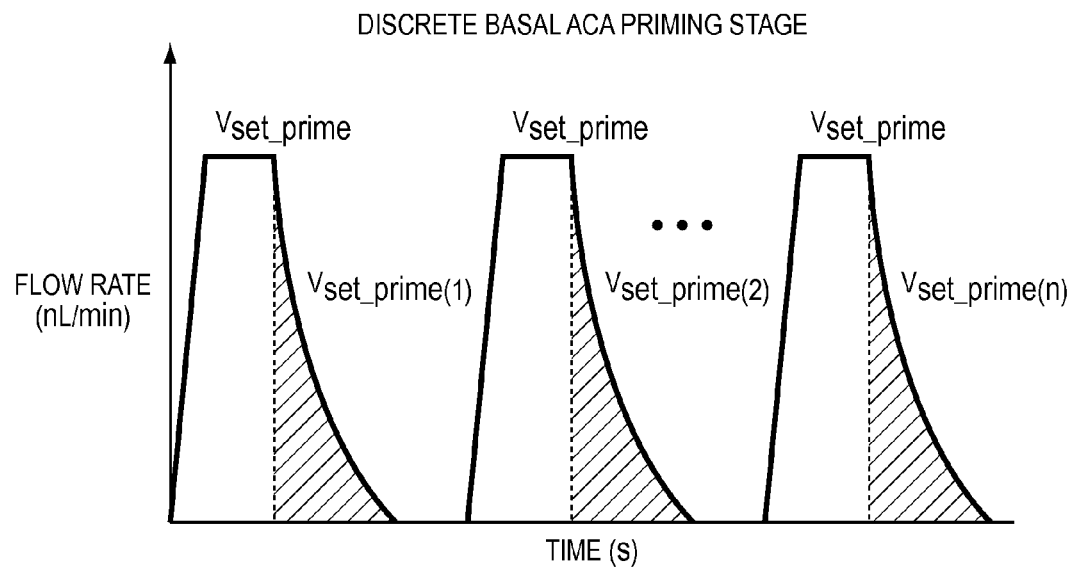
FIG. 6 graphically depicts computation and use of average tail volumes in a compensating flow scheme at the priming stage.

In one embodiment that corrects for these errors, the system controller 112 executes an adaptive control algorithm (ACA) during a priming stage and during a delivery stage. At the priming stage, a number n of predetermined pulses (e.g., 0.05 U/pulse) is scheduled every t minutes. After reaching the target volume for each pulse, the pressure is released and the tail volumes measured. Throughout the priming stage, the system controller 112 (see FIG. 1) collects these tail volumes from a number $N_p$ of pulses to determine an average tail volume. This averaged volume is taken into account in adjusting the time width of the subsequent pulse during the delivery stage. The priming tails are averaged and stored as $V_{tail\_prime\_avg}$ for future usage. This is illustrated in FIG. 6, in which $N_p$ is the number of discrete basal pulses to be delivered during the priming stage, $V_{tail\_prime}(n)$ corresponds to the $n^{th}$ tail volume generated by the $n^{th}$ pulse in the priming stage, and $V_{tail\_prime\_avg}$ corresponds to the average tail volume of the discrete pulses in the priming stage.

Figure 7:
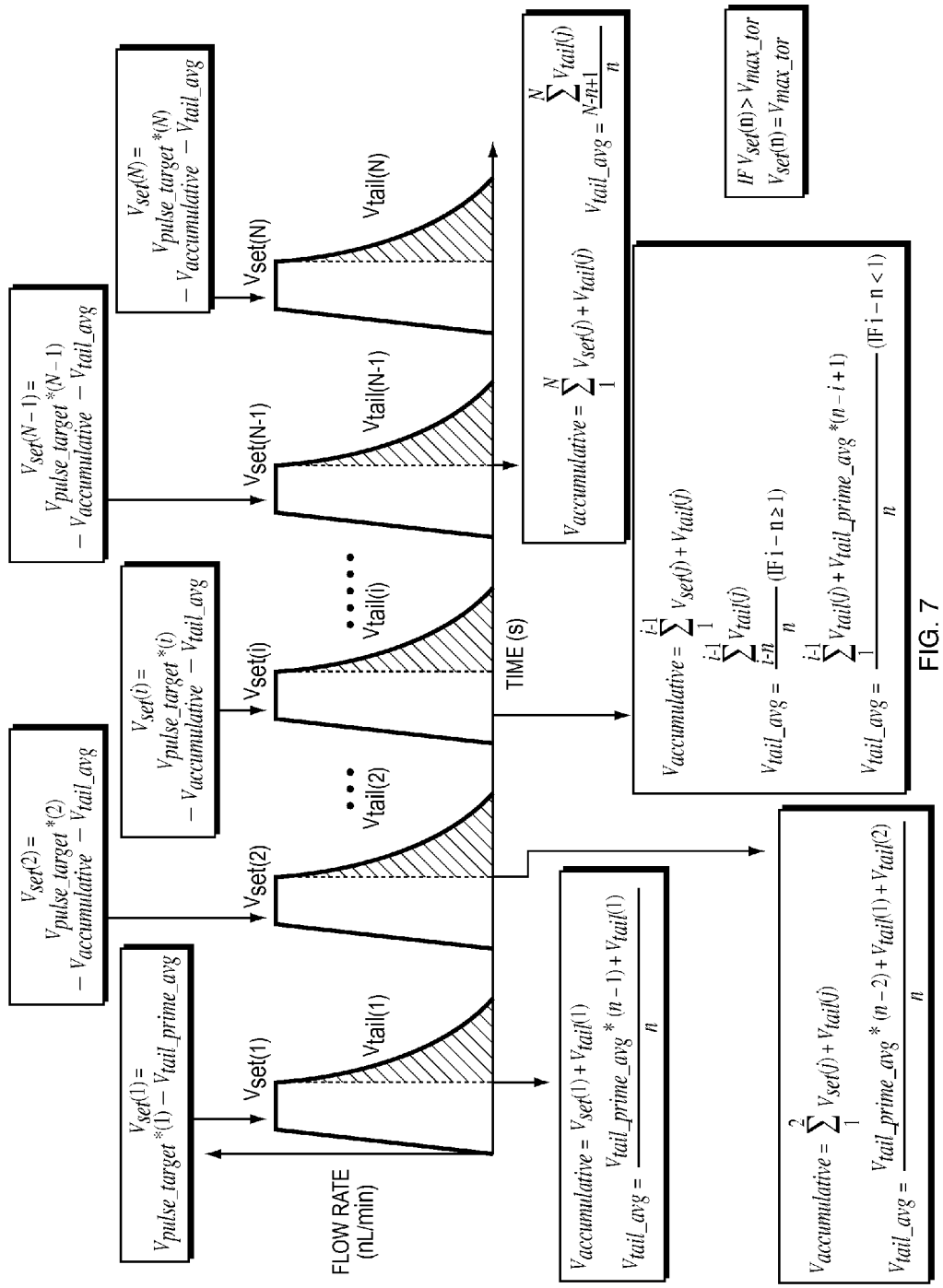
FIG. 7 graphically depicts computation and use of average tail volumes in a compensating flow scheme at the delivery stage.

At the delivery stage, as illustrated in FIG. 7, the discrete basal target volume is adjusted according to the average volume of the previous n tails. The first discrete basal pulse, Set Volume or $V_{set}(n)$, is established as follows. After the tail volumes from the n pulses during the priming stage are averaged, $V_{tail\_prime\_avg}$ is subtracted from $V_{target}$ (the original target volume of the pulse) to give $V_{set}(1)$ (i.e., the adjusted volume for the pulse). In FIG. 7, $V_{pulse\_target}$ is the target volume to be delivered in each pulse, $V_{tail}(n)$ is the tail volume produced by each pulse, $V_{cumulative}$ is the actual cumulative volume delivered over time, and $V_{tail\_avg}$ is the average tail of the previous n discrete basal pulses.

For each subsequent discrete basal pulse, the system uses the previous n tail volumes in calculating the average tail volume to be used in determining the $V_{set}$ for the current discrete basal pulse. For example, if there are three discrete pulses delivered during the priming stage (n=3), $V_{tail\_avg}$ for the first pulse in the delivery stage corresponds to the average of these three previous tails, which in this case is the average of these three tail volumes during the priming stage. Next, the value of $V_{tail\_avg}$ for the second pulse in the delivery stage corresponds to the average of the three previous tails. However, the three previous tails are the second and third discrete basal pulses in the priming stage and the first pulse of the delivery stage. $V_{tail\_avg}$ for the third pulse in the delivery stage corresponds to the average of the third tail in the priming stage and the first and second tails of the delivery stage, and so forth.

A special case arises when $V_{set}$ is negative. This means that there is an overdose from a previous delivery such that the next scheduled pulse should deliver a negative volume to achieve the desired target volume, $V_{target\_overall}$. Of course, drug pumps ordinarily cannot operate to withdraw fluid from the patient. Instead, the system sets $V_{set}$ to 0, which causes the controller 112 to skip the pulse in an effort to correct for a previous over-delivery and achieve the correct overall target volume, $V_{target\_overall}$. Also, to reduce any over-delivery caused by missing multiple pulses, the system can set a maximum tolerance volume to be delivered at each pulse ($V_{max\_tor}$). The $V_{set}$ volume never exceeds $V_{max\_tor}$. If it does, the system controller 112 will coerce $V_{set}$ to be equal to $V_{max\_tor}$. This ensures overall profile stability, and also ensures the absence of dramatic change in overdose and underdose caused by frequent over-delivery and missed pulses.

It should be noted that the tail volume can vary over the lifetime of the pump or even during an operating cycle based on various factors. Accordingly, calibration is typically performed periodically rather than, for example, a single time when the pump is first used. For example, the response of an electrolysis-driven pump to a given input current supplied to the electrolysis electrodes depends on how much liquid is remaining in the drug reservoir and the gas/liquid ratio in the electrolysis chamber. Other factors can cause the response of the pump to change over time including, for example, degradation of electrolysis electrodes, changes in the concentration of the electrolyte in the electrolysis chamber, changes in the flow characteristics of valves in the fluid path, and restrictions that form at the exit port due to tissue growth or some other mechanism.

Similar to discrete basal delivery, continuous basal delivery faces challenges due to the plunger and glass-wall friction. Ordinarily it is not necessary to deliver a pulse pattern in continuous basal delivery (as contrasted with discrete basal delivery), and during continuous pumping, the plunger operates above its stiction range. Nonetheless, a continuous adaptive control algorithm can increase the accuracy of drug delivery by minimizing the errors caused by interaction between the plunger and the glass wall.

In one embodiment, a continuous adaptive control routine continuously monitors the accumulated volume and its deviation from the target volume. The routine sets a time window, $\Delta T$, and maximum tolerable flow rate range, $\Delta Q_{max\_tor}$. The routine calculates the actual volume delivered during $\Delta T$ and its deviation from the target volume. Based on the deviation, a target flow rate, $Q_{set}(2)$, for the next $\Delta T$ window is determined in order to compensate for the error in delivery during the first $\Delta T$ window. The maximum tolerance, $\Delta Q_{max\_tor}$, comes into play when there is too much error in delivery during the first $\Delta T$ and $Q_{set}(2)$ has been raised or decreased beyond the physiological range from $Q_{set\_initial}$. In such case, $Q_{set}(2)$ is coerced to equal $Q_{set\_initial} \pm \Delta Q_{max\_tor}$, depending on the delivery error during previous sampling time. This process repeats throughout continuous basal delivery to ensure the overall stability of the flow profile and delivery accuracy.

There are many ways to raise the $Q_{set}$ for the next $\Delta T$ time window. A simple example is to have only three possible values for $Q_{set}$: $Q_{set\_initial}$, $Q_{set\_initial} + \Delta Q_{max\_tor}$, and $Q_{set\_min} - \Delta Q_{max\_tor}$. In one embodiment, if the cumulative delivered volume did not deviate from the cumulative target volume by more than an acceptable percentage (e.g., 5%) at the end of the sampling period $\Delta T$, then the system will set $Q_{set}$ to $Q_{set\_initial}$, which is the initial flow-rate set point. If the actual delivered volume exceeds the target volume by more than the acceptable percentage (e.g., 5%), $Q_{set}$ is set to $Q_{set} - \Delta Q_{max\_tor}$ for the next time window $\Delta T$. If the actual delivered volume falls below the target volume by more than the acceptable percentage (e.g., 5%), $Q_{set}$ is set to $Q_{set} + \Delta Q_{max\_tor}$ for the next time window $\Delta T$.

Figure 8:
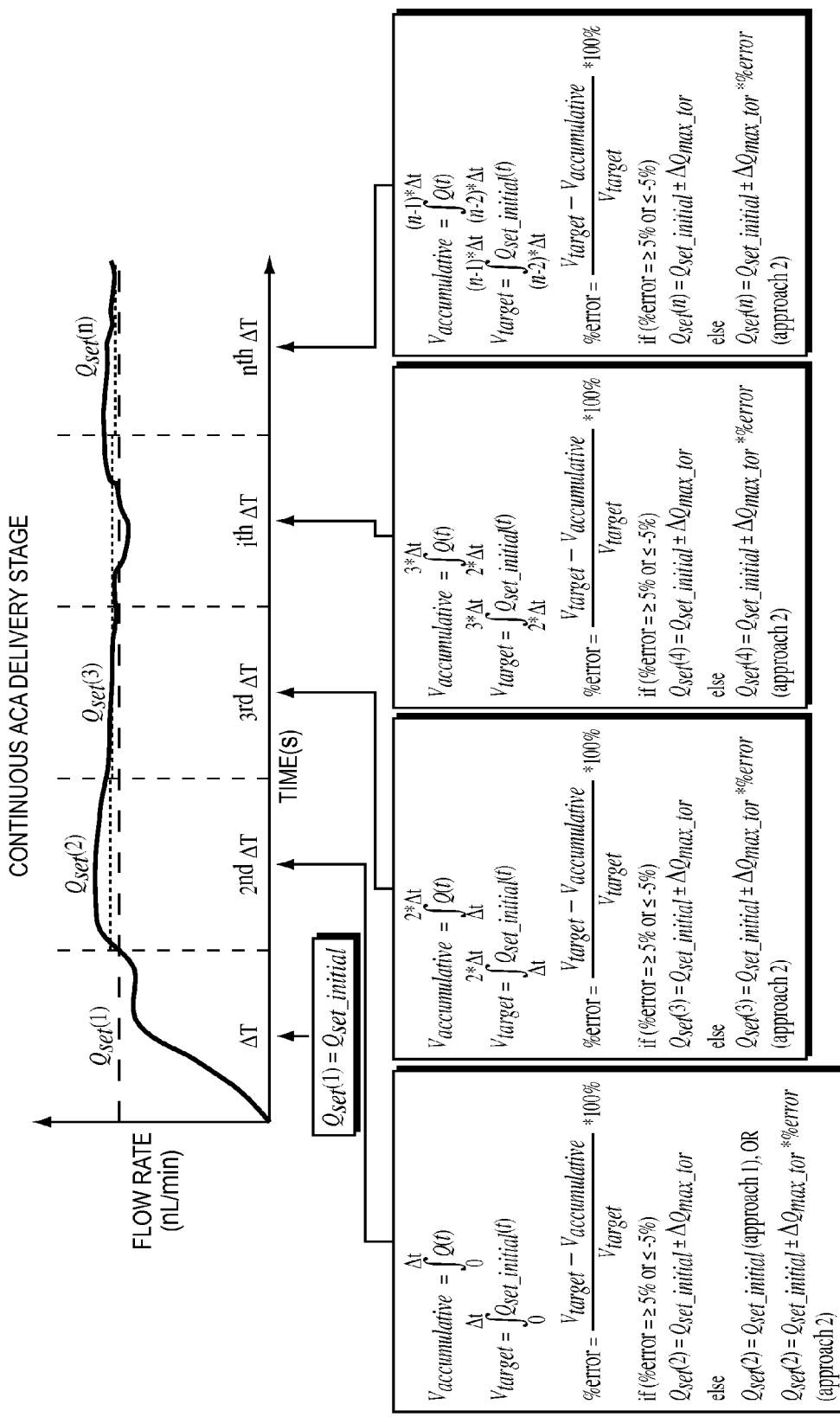
FIG. 8 graphically depicts the operation of an adaptive control algorithm for continuous basal delivery.

In another embodiment, illustrated in FIG. 8, a continuous spectrum of $Q_{set}(n)$ values is used. In the figure, $\Delta T$ is a predefined time window, $Q_{set}(n)$ is the target flow rate during the time window, $Q_{set\_initial}$ is the initial target flow rate (which is also equal to $Q_{set}$, the overall target flow rate), $V_{cumulative}$ is the actual cumulative volume delivered over time, and $V_{target}$ is the target cumulative volume over time, % error represents the error percentage (i.e., the deviation from $V_{target}$) by volume, and $\Delta Q_{max\_tor}$ is the maximum flow rate that $Q_{set}$ cannot exceed.

Each $Q_{set}(n)$ value inversely corresponds to a percentage deviation above or below the target delivery volume from the previous sampling period. If the cumulative delivered volume exceeds the cumulative target volume by more than an acceptable percentage (% error), $Q_{set}(n)$ is set to $Q_{set\_initial} - \%$ error$\times \Delta Q_{max\_tor}$ for the next time window $\Delta T$. If the actual delivered volume falls below the target volume by more than % error, $Q_{set}(n)$ is set to $Q_{set\_initial} + \%$ error$\times \Delta Q_{max\_tor}$ for the next time window $\Delta T$. Once again, the $Q_{set}(n)$ can never go below $Q_{set\_initial} - \Delta Q_{max\_tor}$ or above $Q_{set\_initial} + \Delta Q_{max\_tor}$, or the system will coerce the $Q_{set}(n)$ to be set at $Q_{set\_initial} - \Delta Q_{max\_tor}$ or $Q_{set\_initial} + \Delta Q_{max\_tor}$.

More generally, various algorithms and controllers can be used to adjust pump operation through monitoring and adjustment during time windows. During a time window, for example, a closed-loop control scheme, such as proportional-integral-derivative ("PID") controller, on-off controller, fuzzy logic controller, proportional controller, and/or linear controller can be applied to maintain as constant a target delivery parameter such as flow rate. In the next time window, the constant target delivery parameter can be altered based on the comparison result from the previous time window For example, a PID controller may be used during a timing interval, while a different algorithm, such as the ACA, may be used between time windows to alter the PID controller settings (e.g., the constant target delivery flow rate, the acceptable upper and lower ranges of flow rates, and constants for positional, integral, and derivative calculations). Accordingly, parameters that can be monitored and adjusted include flow rate, pressure, volume, current, and voltage. Moreover, the integration or differentiation of any one or more of these parameters may be monitored and adjusted.

Bolus delivery faces the same accuracy challenges caused by the tail volume as the discrete basal pulses. However, boluses are delivered on demand, and the accuracy of each individual bolus cannot be compensated by another bolus. In the case of insulin delivery, boluses are usually preceded and followed by a background basal delivery; for example, a bolus may be administered just before mealtime, after which insulin is delivered at the background basal rate until the next bolus. In such applications the bolus adaptive control algorithm can be relatively simple, as it may be based solely on tail volume to achieve overall accuracy. In other scenarios, however, the flow profile may be more complex and/or unpredictable; for example, the rate of drug administration may be varied periodically or continuously based on the monitored value of a physiologic, environmental or blood-borne chemical concentration parameter.

In one embodiment, the real-time bolus adaptive control algorithm involves a priming stage and a delivery stage. During the priming stage, a bolus (e.g., 1 U) is delivered and the tail volume is measured until the flow rate reaches zero. This bolus is sufficient in volume to allow the system to pump the flow rate up to its maximum dosing rate (e.g., 30 U/Hr for insulin pump). If the user selects a smaller bolus volume, the peak bolus flow rate may never reach the maximum dosing rate (e.g., 30 U/Hr). If the user selects a large bolus volume, the peak bolus target flow rate can be kept at the maximum dosing rate (e.g., 30 U/Hr) using a flow-sensor-based closed-loop control system as described, for example, in copending application Ser. No. 13/680,828, filed on Nov. 19, 2012 (the entire disclosure of which is hereby incorporated by reference); it simply takes longer to finish the bolus.

Figure 9:
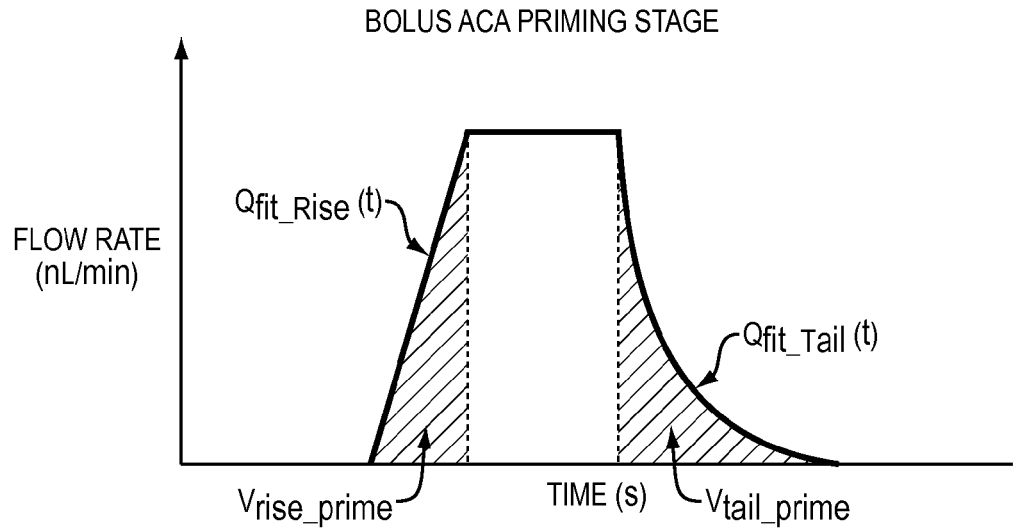
FIG. 9 graphically depicts the operation of an adaptive control algorithm for bolus delivery at the priming stage.

Operation during the priming stage is illustrated in FIG. 9. The white rectangle represents $V_{set\_prime}$, i.e., the desired volume to be delivered. Additional flow during ramp-up ($V_{rise\_prime}$) and during the tail ($V_{tail\_prime}$) is modeled by fitted curves $Q_{fit\_Rise}(t)$ (flow rate vs. time during the ramp up stage) and $Q_{fit\_Rise}(t)$ (representing the tail after $V_{set\_prime}$ has completed). The areas under these fitted curves correspond to $V_{rise\_prime}$ (the volume delivered during ramp-up) and $V_{tail\_prime}$ (the volume delivered during the tail segment). After obtaining the tail volume information and its curve, interpolation can be used to predict the tail volume for different boluses with different potential peak flow rates. The interpolated curve and the peak flow rate at the end of the bolus can be used to predict the tail volume.

Figure 10A:
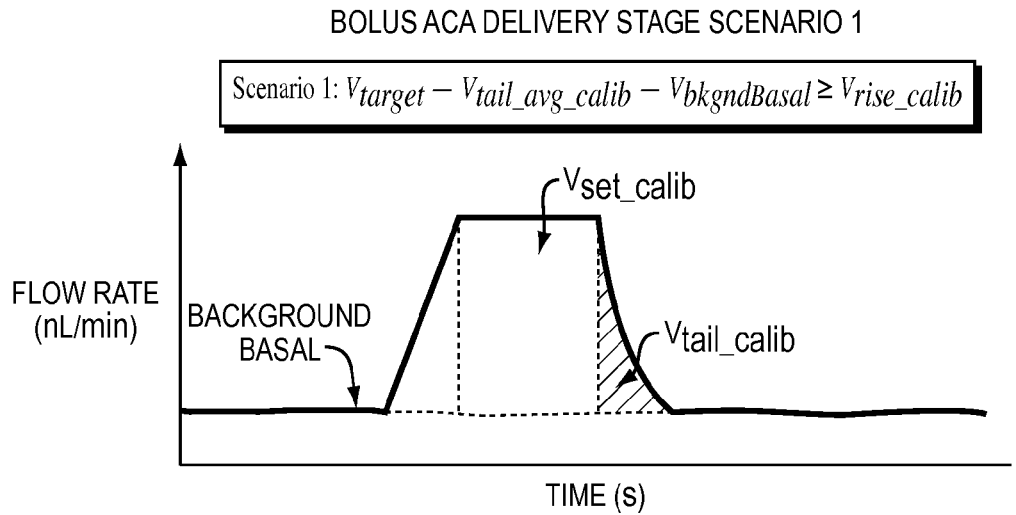
FIG. 10A graphically depicts the delivery stage of the bolus algorithm.
Figure 10B:
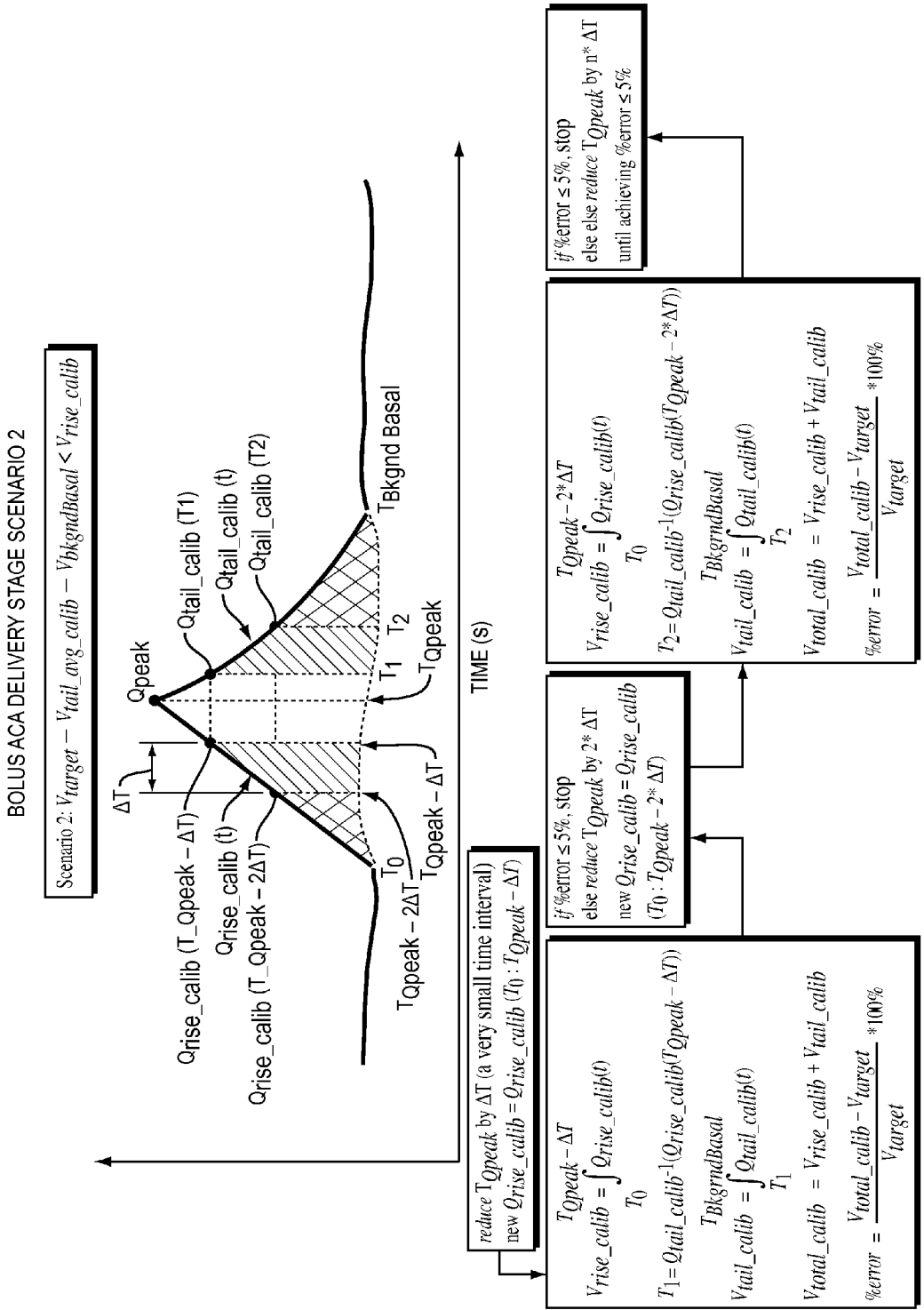
FIG. 10B graphically depicts the delivery stage of the bolus algorithm in a situation where the bolus volume is small and the peak flow rate never reaches the maximum dosing rate.

Two delivery-stage scenarios are illustrated, respectively, in FIGS. 10A and 10B. In FIG. 10A, the flow pattern corresponds to that shown in FIG. 9, with a peak flow rate is that is substantially constant (flat). A calibrated tail volume $V_{tail\_avg\_calib}$ is used to calculate the actual delivery bolus volume, which is equal to the difference between the target volume $V_{target}$ and the total predicted tail volume (including the background basal cumulative volume); thus, the calibrated set volume $V_{set\_calib}$ is equal to $V_{target}-V_{tail\_avg\_calib}-V_{BkgndBasal}$. The total bolus volume $V_{total}$ actually delivered is equal to $V_{set\_calib}+V_{tail\_calib}$, where $V_{tail\_calib}$ is the actual run-time tail volume (this time ignoring the background basal cumulative volume).

If the bolus volume is small and the peak flow rate never reaches the maximum dosing rate (e.g., 30 U/Hr) before the target bolus volume has been delivered, a curve-fitting technique may be used to predict the peak flow rate as illustrated in FIG. 10B; here the tail volume is estimated between the predicted peak flow rate and the (actual) background basal flow rate. This can give a very accurate prediction of the tail volume, and during the actual delivery this is used to compensate for the effect of the tail effect. In FIG. 10B, $T_0$ is the bolus start time; $T_{Qpeak}$ is the time at which the bolus reaches the maximum peak set flow rate $Q_{peak}$; $\Delta T$ is an adjustment time set to create a fitted curve as shown in FIG. 10B (and may range from, e.g., 1 ms to 1 s depending on the application in order to balance acceptable error and power restrictions that determine the sample rate and, in turn, the duration of the sample time interval); $T_1$ is the time when $Q_{tail\_calib}(t)$ (the fitted tail curve) reaches $Q_{tail\_calib} \times (T_{Qpeak}-\Delta T)$; $T_2$ is the time when $Q_{tail\_calib}(t)$ reaches $Q_{tail\_calib} \times (T_{Qpeak}-2\Delta T)$; and $T_{BkgndBasal}$ is the time when $Q_{tail\_calib}(t)$ reaches the background basal flow rate.

After delivery is complete, the tail volume is stored in memory along with the estimated (fitted) curve. This historical tail behavior may be used to predict the tail volume for future boluses delivered from the same cartridge.

As discussed above, the priming stage is typically employed to evacuate air from the fluid path of the device, preventing air and/or debris from being injected into the target site, and also wets any sensors in the fluid path. Because of the faults that priming is designed to remediate, calibrating during the priming stage may not be ideal. In some embodiments, therefore, a non-therapeutic dose is dispensed by the pump following priming, and this dose is used instead of or in addition to the priming stage for calibration purposes. For example, it may be necessary to use the non-therapeutic dose for calibration if the sensor used therefor is in the fluid path and must be wet to operate properly. As used herein, the term "non-therapeutic dose" means a volume of drug less than a therapeutic dose, and in some embodiments, a dose small enough to avoid any therapeutic effect or clinically significant effect.

It should be emphasized that, although the preceding discussion has focused on a single target dosage, this need not be the case. Many medications, including monoclonal antibodies, require dosages based on the patient's weight or the severity of the diseases. Accordingly, pumps in accordance herewith may have the ability to deliver a range of target dosages; in some embodiments, a dose-selection mechanism is incorporated—for example, a dose-selection interface may allow the user to select the dosage, which is programmed into memory within the controller 112. This interface may be or include a switch, dial, buttons, touch screen, or a variety of user-interface components. The dosage may also be pre-set by the manufacturer, clinician, pharmacist, or other non-patient entity, and locked for security purposes.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A drug pump device comprising:
   a drug reservoir;
   an exit member for fluidically connecting the reservoir with a drug injection site;
   a sensor;
   an electrolysis pump comprising a pump chamber in mechanical communication with the drug reservoir via an intervening displacement member, the electrolysis pump being operable to exert a pressure to drive the displacement member toward the exit member and thereby force therethrough fluid in the drug chamber; and
   control circuitry for (i) storing a target delivered volume over a specified time, (ii) operating the electrolysis pump to force fluid from the drug reservoir into the exit member in pulses having a time window defined by a pump-start time when pumping begins and a pump-stop time when the pump is shut off, the time window corresponding to the target delivered volume at a predetermined flow rate, (iii) based on signals received from the sensor, measuring a volume of fluid through the exit member resulting from a pulse, the measured volume including a pulse volume through the exit member during the pulse and an additional tail volume through the exit member after the pulse, and (iv) adjusting the pulse time window based on the measured pulse volume and tail volume to conform collectively to the target delivered volume.

2. The device of claim 1, wherein the sensor is at least one pressure sensor.

3. The device of claim 1, wherein the sensor is at least one flow sensor.

4. The device of claim 1, wherein the sensor comprises at least one flow sensor and at least one pressure sensor.

5. The device of claim 1, wherein the target delivered volume corresponds to a single bolus, the control circuitry causing measuring to occur during a priming stage and causing adjustment to occur during a delivery stage.

6. The device of claim 1, wherein the control circuitry causes the target delivered volume to be dispensed through the exit member over a sequence of time-separated pulses occurring over a time interval, the control circuitry causing measuring to occur during a first time interval and causing adjustment to occur during a second time interval following the first time interval.

7. The device of claim 6, wherein the adjustment is based on the measured pulse volume and tail volume from a plurality of pulses.

8. The device of claim 1, wherein the intervening displacement member comprises a piston, a diaphragm, a bladder, or a plunger.

9. A method of controlling an actual delivery volume of fluid in a drug pump device comprising a drug reservoir, an exit member for fluidically connecting the reservoir with a drug injection site, and an electrolysis pump operable to force fluid from the drug reservoir into the exit member in pulses each having a time window defined by a pump-start time when pumping begins and a pump-stop time when the pump is shut off, the time window corresponding to a target delivered volume at a predetermined flow rate, to conform to a target delivery volume, the method comprising:
  measuring a volume of fluid through the exit member resulting from a pulse, the measured volume including (i) a pulse volume through the exit member during the pulse and (ii) an additional tail volume through the exit member after the pulse; and
  adjusting the pulse time window based on the measured pulse volume and tail volume to conform collectively to the target delivered volume.

10. The method of claim 9, wherein the measurement is made with at least one pressure sensor.

11. The method of claim 9, wherein the sensor is at least one flow sensor.

12. The method of claim 9, wherein the target delivered volume corresponds to a single bolus, the measuring step occurring during a priming stage and the adjusting step occurring during a delivery stage.

13. The method of claim 9, wherein the target delivered volume is dispensed through the exit member over a sequence of time-separated pulses occurring over a time interval, the measuring step occurring during a first time interval and the adjusting step occurring during a second time interval following the first time interval.

14. The method of claim 13, wherein the adjusting step is based on the measured pulse volume and tail volume from a plurality of pulses.

* * * * *